US012590054B2

(12) United States Patent
Nanovskaya et al.

(10) Patent No.: US 12,590,054 B2
(45) Date of Patent: Mar. 31, 2026

(54) USE OF D9-METHADONE FOR POSTOPERATIVE PAIN RELIEF

(71) Applicant: Board of Regents, The University of Texas System, Austin, TX (US)

(72) Inventors: Tatiana N. Nanovskaya, League City, TX (US); Jun-Ho La, Galveston, TX (US); Mahmoud S. Ahmed, Galveston, TX (US); Jigong Wang, League City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 7 days.

(21) Appl. No.: 18/087,350

(22) Filed: Dec. 22, 2022

(65) Prior Publication Data

US 2024/0116851 A1 Apr. 11, 2024

Related U.S. Application Data

(60) Provisional application No. 63/293,261, filed on Dec. 23, 2021.

(51) Int. Cl.
*C07C 225/06* (2006.01)
*A61K 31/137* (2006.01)
*A61K 45/06* (2006.01)
*A61P 25/04* (2006.01)
*C07B 59/00* (2006.01)

(52) U.S. Cl.
CPC .......... *C07C 225/06* (2013.01); *A61K 31/137* (2013.01); *A61K 45/06* (2013.01); *A61P 25/04* (2018.01); *C07B 59/001* (2013.01)

(58) Field of Classification Search
CPC ....... A61K 31/137; A61K 45/06; A61P 25/04; C07B 59/001; C07C 225/06
See application file for complete search history.

(56) References Cited

FOREIGN PATENT DOCUMENTS

EP 2943489 4/2018
WO WO-2016185468 A1 * 11/2016 ........... A61K 31/164

OTHER PUBLICATIONS

Kushner, D J et al. "Pharmacological uses and perspectives of heavy water and deuterated compounds." Canadian journal of physiology and pharmacology vol. 77,2 (1999): 79-88. (Year: 1999).*
Nowak, Karolina, et al. "Quantification of Methadone and Its Metabolites: EDDP and EMDP Determined in Autopsy Cases Using LC-ms/MS." Journal of Forensic Sciences, vol. 66, No. 3, Jan. 29, 2021, pp. 1003-1012, doi:10.1111/1556-4029.14674. (Year: 2021).*
Gérardy et al. Journal of Labelled Compounds and Radiopharmaceuticals—vol. XXII, No. 1, 1985 (Year: 1985).*
Kumar, Clinical Medicine Insights: Therapeutics. 2:299-305, 2010.
Holme et al., Mutagenesis. 4(5):355-60, 1989.
Pang et al., J Labelled Comp Radiopharm. 60(9):401-409, 2017.
Concert Pharmaceuticals presents positive 48-week results from Phase 2 clinical trail of CTP-499 in diabetic kidney disease. 2014.
Harbeson and Tung, Medchem News. 24(2):8-22, 2014.
Faggiano et al., Cochrane Database Syst Rev. (3):CD002208, 2003.
Vocci et al., Am J Psychiatry. 162(8):1432-40, 2005.
Adelson et al., J Addict Dis. 26(1):15-26, 2007.
Hiltunen et al., Psychopharmacology (Berl). 143(4):385-93, 1999.
Holmstrand et al., Clin Pharmacol Ther. 23(2):175-80, 1978.
Tennant, Am J Psychiatry. 144(10):1349-50, 1987.
George and Braithwaite, J Anal Toxicol. 23(2):81-5, 1999.
Moolchan et al., J Addict Dis. 20(2):55-73, 2001.
Kharasch et al., Clin Pharmacol Ther. Sep 76(3):250-69, 2004.
Totah et al., J Pharmacol Exp Ther. 321(1):389-99, 2007.
Totah et al., Anesthesiology. 108(3):363-74, 2008.
Chang et al., Basic Clin Pharmacol Toxicol. 108(1):55-62, 2011.
Crettol et al., Clin Pharmacol Ther. 78(6):593-604, 2005.
Crettol et al., Clin Pharmacol Ther. 80(6):668-81, 2006.
Wang et al., OMICS. 17(10):519-26, 2013.
Shiran et al., Br J Clin Pharmacol. 67(1):29-37, 2008.
Nelson and Trager, Drug Metab Dispos. 31(12):1481-98, 2003.
Guengerich, J Labelled Comp Radiopharm. 56(9-10):428-31, 2013.
Guengerich, Methods in enzymology. 596:217-238, 2017.
Pirali et al., J Med Chem. 62(11):5276-97, 2019.
Kristensen et al., Life sciences. 56(2):PI45-50, 1995.
Olsen et al., Clin Pharmacol Ther. 21(2):147-57, 1977.
McCance-Katz, Addiction (Abingdon, England). 106(4):687-8, 2011.
Zünkler and Wos-Maganga, Cardiovascular toxicology. 10(3):161-5, 2010.
Krantz et al., Annals of internal medicine. 150(6):387-95, 2009.
Eap et al., European journal of clinical pharmacology. 50(5):385-9, 1996.
Eap et al., Archives of general psychiatry. 55(1):89-90, 1998.
Gerber et al., Chirality. 16(1):36-44, 2004.
Maltais et al., J Med Chem. 52(24):7993-8001, 2009.
Jacques et al., 2021 not the same article provided, but similar topic and same author: (PXL-065).
Wang et al., Psychopharmacology (Berl). 173(1-2):132-8, 2004.
Elison et al., Science. 134(3485):1078-9, 1961.
Hsia et al., Science. 193(4252):498-500, 1976.
MMWR Morb Mortal Wkly Rep. 61(26):493-7, 2012.
Kharasch, Anesth Analg. 112(1):13-6, 2011.
Gottschalk et al., Anesth Analg. 112(1):218-23, 2011.
Cai et al., J Clin Invest. 129(7):2730-2744, 2019.

* cited by examiner

*Primary Examiner* — Sarah Pihonak
*Assistant Examiner* — Donna M Nestor

(57) ABSTRACT

Certain embodiments are directed to the use of d9-methadone as an alternative formulation for methadone, the $d_9$-methadone having an improved absorption-distribution-metabolism-excretion profile, analgetic efficacy, and safety for the management of pain following injury such as trauma, disease, and surgery.

15 Claims, 6 Drawing Sheets

USE OF D9-METHADONE FOR POSTOPERATIVE PAIN RELIEF

RELATED APPLICATIONS

This application claims priority to U.S. Provisional Application 63/293,261 filed Dec. 23, 2021, which is incorporated herein by reference in its entirety.

STATEMENT OF FEDERALLY SPONSORED RESEARCH

None.

FIELD OF THE INVENTION

Embodiments of the invention are directed generally to the field of medicine, and more particularly to pain management.

BACKGROUND OF THE INVENTION

Deuterium is a naturally occurring, stable, non-radioactive hydrogen isotope. In recent years, the use of deuterated compounds in the clinical development of medications has become a fast-growing field. The current reintroduction of deuterated medications is associated with the proven safety of deuterium (Schoeller 1988; Dufner and Previs, 2003; Gant, 2014), improved pharmacokinetic properties (Schneider et al., 2011; Manley et al., 2013; Xu et al., 2014; Guo et al., 2015; Pang et al., 2017; Velthuisen et al., 2013; Jiang et al., 2016; Stringer et al., 2014; Harbeson et al., 2017), improved tolerability (Claassen et al., 2017), improved efficacy, and decreased adverse effects (Pang et al., 2017; Garay and Grossberg et al., 2017; Harbeson et al., 2014) of the deuterated compounds compared to the parent compounds.

Methadone is a drug for opioid use disorder (OUD) treatment and has greater analgesic potency, reduced tolerance development, and lesser euphoric effects than morphine (Cai et al., 2019; Altarifi et al., 2015; Enguist et al., 2012) making it a unique opioid compound that could help end long-term addiction directly as an OUD therapeutic and indirectly as a replacement for the current first-line opioid analgesics. However, the complex absorption-distribution-metabolism-excretion (ADME) profile of methadone has limited such a potential.

There remains a need for additional forms of methadone and/or methadone derivatives and additional therapeutic uses of the same.

SUMMARY OF THE INVENTION

As a solution to the non-optimal pharmacologic properties of methadone the inventors have discovered the benefits of $d_9$-methadone. Certain embodiments are directed to the use of $d_9$-methadone as an alternative formulation for methadone, the $d_9$-methadone having an improved absorption-distribution-metabolism-excretion profile, analgetic efficacy, and safety for the management of pain following injury such as trauma, disease, and surgery.

Certain embodiments are directed to a deuteriated methadone having the structure of Formula I, where D is deuterium Formula I

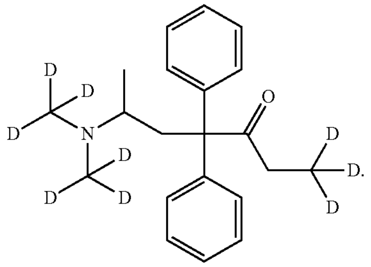

Certain embodiments are directed to methods for treatment of pain in a subject comprising administering the compound of Formula I. The compound or a composition comprising the compound can be administered orally, nasally, transcuteneously, subcutaneously, intramuscularly, intravenously, intrathecaly or epidurally, sublingually, transbuccally, transsclerolly, or intraosseously. The composition can include a pharmacologically effective amount of an opioid antagonist. In certain aspects, the opioid antagonist is naloxone or naltrexone. The composition can further include a nonopioid component and its pharmaceutically acceptable salts. In certain aspects the pain is both neuropathic and/or somatic in origin. The subject can be a mammal, and in particular a human.

Other embodiments are directed to methods for treatment of addiction in a subject comprising administering the compound of Formula I or a composition comprising a compound of Formula I. The compound or composition comprising the compound can be administered orally, nasally, transcuteneously, subcutaneously, intramuscularly, intravenously, intrathecaly or epidurally, sublingually, transbuccally, transsclerolly, or intraosseously. In certain aspects the composition can include or the compound can be co-administered with a pharmacologically effective amount of an opioid antagonist. 13. A method according to claim 12, wherein the opioid antagonist is naloxone or naltrexone. The composition can further include a nonopioid component and its pharmaceutically acceptable salts. In certain aspects the subject is a mammal, in particular a human.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The term "methadone" (6-(dimethylamino)-4,4-diphenylheptan-3-one) as used herein is a synthetic opioid agonist used for opioid maintenance therapy in opioid dependence and for chronic pain management. Methadone has the following chemical structure:

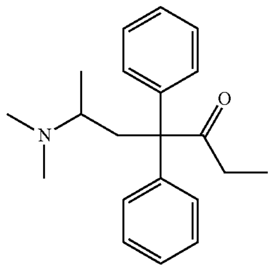 [SMILES: CCC(=O)C(CC(C)N(C)C)(c1ccccc1)c1ccccc1]

methadone

The term "$d_3$-methadone" as used herein is a deuterated variant of methadone having the following chemical structure:

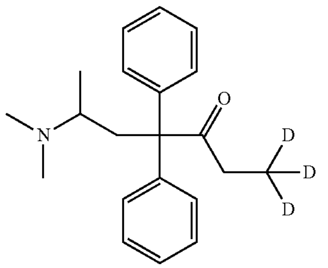 [SMILES: [2H]C([2H])([2H])CC(=O)C(CC(C)N(C)C)(c1ccccc1)c1ccccc1]

$d_3$-methadone, D is deuterium

The compound "$d_9$-methadone" is a deuterated variant of methadone having the following chemical structure:

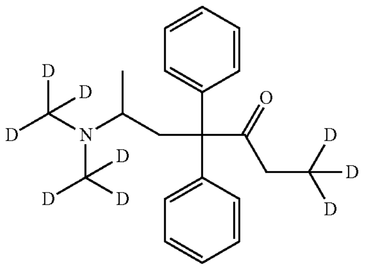 [SMILES: [2H]C([2H])([2H])CC(=O)C(CC(C)N(C([2H])([2H])[2H])C([2H])([2H])[2H])(c1ccccc1)c1ccccc1]

$d_9$-methadone, D is deuterium

The compound 2-ethylidine-1,5-dimethyl-3,3-diphenylpyrrolidine (EDDP) is a metabolite of methadone having the following structure:

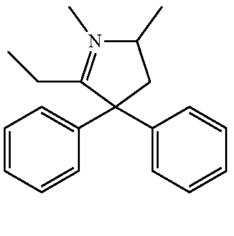

methadone metabolite, 2-ethylidine-1,5-dimethyl-3,3-diphenylpyrrolidine (EDDP)

The compound $d_3$-EDDP is a deuterated metabolite of $d_3$-methadone having the following structure:

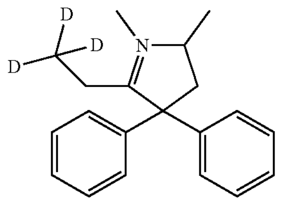

$d_3$-EDDP, D is deuterium

The compound $d_6$-EDDP is a deuterated metabolite of $d_9$-methadone having the following structure:

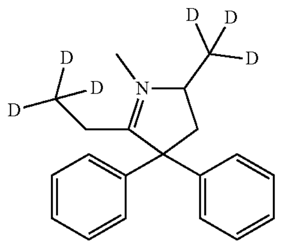

d6 EDDP, D is deuterium

Deuterium (D) is a naturally occurring, stable, non-radioactive hydrogen isotope. In recent years, the use of deuterated compounds in the clinical development of medications has become a fast-growing field.

"Reducing incidence" of chronic pain and/or a symptom associated with chronic pain means any of reducing severity (which can include reducing need for and/or amount of (e.g., exposure to) other drugs and/or therapies generally used for these conditions), duration, and/or frequency.

"Ameliorating" chronic pain and/or a symptom associated with chronic pain means a lessening or improvement of one or more symptoms of chronic pain and/or symptoms associated with chronic pain as compared to not administering $d_9$-methadone. "Ameliorating" also includes shortening or reduction in duration of a symptom.

"Palliating" chronic pain and/or a symptom associated with chronic pain means lessening the extent of one or more undesirable clinical manifestations of chronic pain in an individual or population of individuals treated with $d_9$-methadone in accordance with the invention.

As used therein, "delaying" the development of chronic pain means to defer, hinder, slow, retard, stabilize, and/or postpone progression of chronic pain and/or a symptom associated with chronic pain. This delay can be of varying lengths of time, depending on the history of the disease and/or individuals being treated. As is evident to one skilled in the art, a sufficient or significant delay can, in effect, encompass prevention, in that the individual does not develop chronic pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

An "individual" or "subject" is a vertebrate, preferably a mammal, more preferably a human. Mammals include, but are not limited to, farm animals (such as cows), sport animals, pets (such as cats, dogs and horses), primates, mice and rats.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

As used herein, the term "coadminister" refers to administration of two or more agents within a 24 hour period of each other, for example, as part of a clinical treatment regimen. In other embodiments, "coadminister" refers to administration within 2 hours of each other. In other embodiments, "coadminister" refers to administration within 30 minutes of each other. In other embodiments, "coadminister" refers to administration within 15 minutes of each other. In other embodiments, "coadminister" refers to administration at the same time as multiple formulations that are administered by the same or different routes.

"Coformulation" refers to two or more active agents in a single formulation.

Certain embodiments of the present invention are directed to a medicament for the prevention and/or treatment of chronic pain and/or symptoms of chronic pain and methods for prevention and/or treatment of chronic pain and/or symptoms of chronic pain in an individual.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps) but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION

Figure 1:
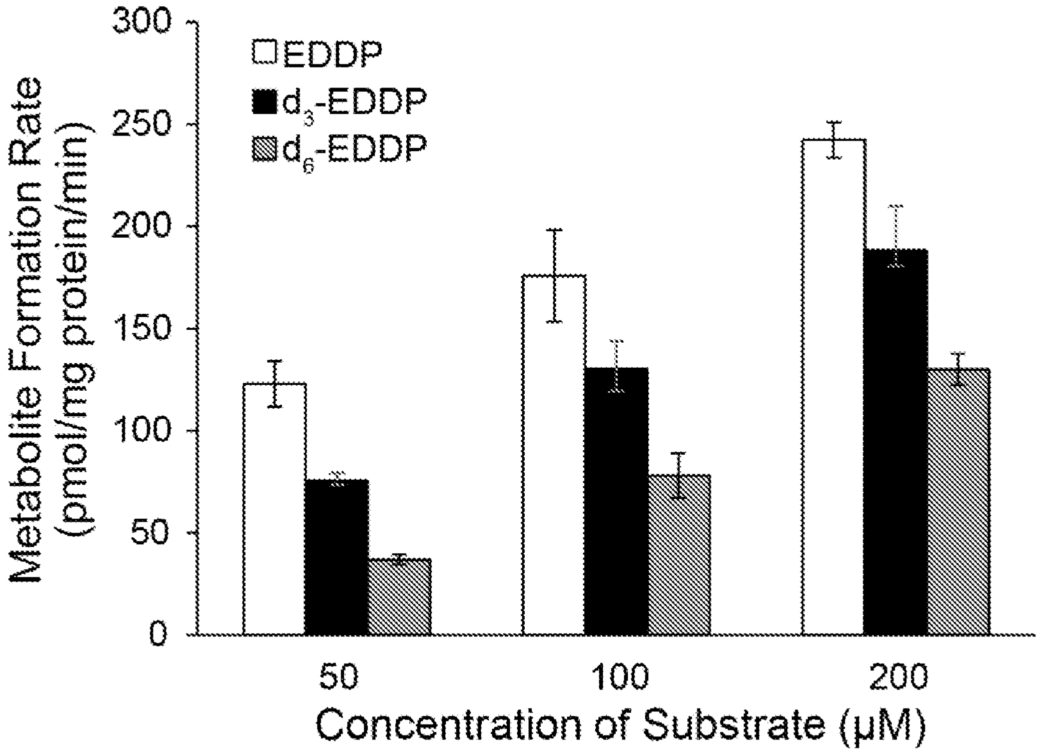
FIG. 1. N-demethylation of methadone to EDDP, $d_3$-methadone to $d_3$-EDDP, and $d_9$-methadone to $d_6$-EDDP.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to imply that the scope of the disclosure, including the claims, is limited to that embodiment.

I. DEUTERATED METHADONE

Currently, methadone is one of the primary options for the medication-assisted therapy of opioid use disorder (Alinejad et al., *Iranian journal of medical sciences.* 42(4):327-46, 2017) and for alleviating chronic pain (Kumar, *Clinical Medicine Insights: Therapeutics.* 2:299-305, 2010). In the last two decades, despite an increase in the use, abuse, misuse, as well as fatal and non-fatal overdoses involving prescription opioids, only one novel opioid derivative, tapentadol, was introduced for therapeutic use, highlighting the need for safe and efficacious opioid analgesics.

The improved pharmacokinetic profile of deuterated compounds can lead to alleviation of side effects either from enhanced metabolic stability of the parent drug and decreased formation of reactive metabolites (O'Driscoll, *Chemistry & Industry.* 24-26, 2009; Holme et al., *Mutagenesis.* 4(5):355-60, 1989) or from increased half-life of the compounds with little if any effects on $C_{max}$ thus reducing $C_{max}$-driven side effects (Pang et al., *J Labelled Comp Radiopharm.* 60(9):401-409, 2017; Concert Pharmaceuticals presents positive 48-week results from Phase 2 clinical trail of CTP-499 in diabetic kidney disease. 2014; Harbeson and Tung, *Medchem News.* 24(2):8-22, 2014). For example, the high rates of adverse events (sedation/somnolence, fatigue, depression, akathisia, nausea) associated with the administration of tetrabenazine to treat chorea associated with Huntington's disease is attributed in part to the $C_{max}$ levels of the parent compound. On the other hand, the pharmacokinetic profile of deuterated tetrabenazine allows for the achievement of similar exposures with a lower $C_{max}$ at a lower dose, thus reducing chorea and minimizing the adverse events of tetrabenazine (Harbeson and Tung, *Medchem News.* 24(2):8-22, 2014). Since methadone does not produce active metabolites, and both analgesic and adverse effects are attributed to the parent compound, it appears that potential clinical benefits of methadone deuteration could include similar systemic exposure with increased trough levels and a decreased $C_{max}$ at a lower dose. This could result in lower side effects.

The deuterium kinetic isotope effect (DKIE) on the metabolic profile of racemic compounds—including the effects of deuteration on the activity of different CYP450 enzymes, the transporter P-glycoprotein (P-gp), pharmacological activity, and the safety of racemic compounds—is unpredictable. Embodiments of this application are directed deuterated methadone with improved properties. Information provided herein demonstrate how the deuteration of methadone affects the: (1) stereoselective biotransformation; (2) interaction with the transporter P-gp; (3) pharmacokinetic properties and tissue distribution; (4) acute toxicity; (5) analgesic activity; and (6) abuse liability.

Effect of deuteration on the activity of enzymes involved in stereoselective biotransformation of $d_9$-methadone and its transport by P-glycoprotein. Existing data from controlled clinical trials show that a reduction in illicit drug consumption can be achieved by using a wide range of daily doses of methadone from 10 to 300 mg (Faggiano et al., Cochrane Database Syst Rev. (3):CD002208, 2003; Vocci et al., Am J Psychiatry. 162(8):1432-40, 2005). The correlation between methadone dosage and its plasma concentrations is low to moderate (Adelson et al., J Addict Dis. 26(1):15-26, 2007; Hiltunen et al., Psychopharmacology (Berl). 143(4):385-93, 1999). Furthermore, there is high (up to 17-fold) inter-individual variation in the plasma concentration of methadone among patients taking the same dose of medication (Holmstrand et al., Clin Pharmacol Ther. 23(2):175-80, 1978; Tennant, Am J Psychiatry. 144(10):1349-50, 1987), indicating that there is great variance among individuals with respect to methadone metabolism (George and Braithwaite, J Anal Toxicol. 23(2):81-5, 1999; Moolchan et al., J Addict Dis. 20(2):55-73, 2001). While CYP2B6 is the major hepatic enzyme responsible for the N-demethylation of methadone in vitro (Kharasch et al., Clin Pharmacol Ther. September 76(3):250-69, 2004; Gerber et al., Chirality. 16(1):36-44, 2004) as well as in vivo (Totah et al., J Pharmacol Exp Ther. 321(1):389-99, 2007; Totah et al., Anesthesiology. 108(3):363-74, 2008; Chang et al., Basic Clin Pharmacol Toxicol. 108(1):55-62, 2011), other enzymes such as CYP2D6, CYP3A5, CYP2C9, CYP2C19, and CYP3A4 (Totah et al., Anesthesiology. March 108(3): 363-74, 2008; Crettol et al., Clin Pharmacol Ther. 78(6): 593-604, 2005; Crettol et al., Clin Pharmacol Ther. 80(6): 668-81, 2006; Wang et al., OMICS. 17(10):519-26, 2013; Shiran et al., Br J Clin Pharmacol. 67(1):29-37, 2009) are also important in the metabolism of methadone.

In general, deuterium substitution slows CYP450-mediated biotransformation (Nelson and Trager, *Drug Metab Dispos.* 31(12):1481-98, 2003; Guengerich, *J Labelled Comp Radiopharm.* 56(9-10):428-31, 2013; Guengerich, *Methods in enzymology.* 596:217-238, 2017) because C-D bonds are shorter and more stable to oxidative processes than C—H bonds (Pirali et al., *J Med Chem.* 62(11):5276-97, 2019). Deuterium has a 2-fold higher mass than hydrogen, leading to a reduced vibrational stretching frequency of the C-D bond compared to the C—H bond. Therefore, the activation energy required for reaching the transition state for bond cleavage is greater for C-D than C—H, and the reaction rate is slower (Pirali et al., *J Med Chem.* 62(11): 5276-97, 2019). However, there is a possibility that while metabolism of the drug is decreased at the site of deuterium incorporation, at another site the metabolism could be enhanced, as was shown for maraviroc (Pirali et al., *J Med Chem.* 62(11):5276-97, 2019). Also, the magnitude of these changes depends on the rate-limiting steps in a particular enzyme reaction, which can reverse the consequences of deuteration (Nelson and Trager, *Drug Metab Dispos.* 31(12): 1481-98, 2003; Guengerich, *J Labelled Comp Radiopharm.* 56(9-10):428-31, 2013; Guengerich, *Methods in enzymology.* 596:217-238, 2017). Thus, the effect of deuterium incorporation on the activity of each of these enzymes CYP2B6, CYP2D6, CYP3A5, CYP2C9, CYP2C19, and CYP3A4 in the biotransformation of $d_9$-methadone must be determined.

Clinically, methadone is administered as a racemic mixture of (R)- and (S)-methadone, and N-demethylation of methadone is stereoselective. The R-enantiomer has high affinity towards μ-opioid receptors, and numerous studies have demonstrated that the R-enantiomer of methadone is responsible for the drug's activity (Kristensen et al., *Life sciences.* 56(2):P145-50, 1995; Olsen et al., *Clin Pharmacol Ther.* 21(2):147-57, 1977). The S-enantiomer has low affinity for opioid receptors (McCance-Katz, *Addiction* (Abingdon, England). 106(4):687-8, 2011), but it binds to human Ether-a-go-go Related Gene (hERG) channels in cardiac myocytes (Zünkler and Wos-Maganga, *Cardiovascular toxicology.* 10(3):161-5, 2010). The latter has been associated with cardiac adverse effects of methadone such as arrhythmias, particularly torsade de pointes (Krantz et al., *Annals of internal medicine.* 150(6):387-95, 2009). It should be noted that in addition to large plasma variations in methadone concentrations, there is also a large variability in the R/S ratio, ranging from 0.63 to 2.4 (Eap et al., *European journal of clinical pharmacology.* 50(5):385-9, 1996; Eap et al., *Archives of general psychiatry.* 55(1):89-90, 1998). While CYP2B6 exhibits a greater preference for the metabolism of S-methadone than for R-methadone (Crettol et al., *Clin Pharmacol Ther.* 78(6):593-604, 2005), CYP2C19 preferentially metabolizes the active R-enantiomer (Gerber et al., *Chirality.* 16(1):36-44, 2004). Since the incorporation of deuterium in racemic compounds could affect the stability of one of the enantiomers (Maltais et al., *J Med Chem.* 52(24): 7993-8001, 2009; Jacques et al., DRX-065, the Deuterated (R)-Enantiomer of Pioglitazone, as a Nonalcoholic Steatohepatitis (NASH) Drug Candidate: Preclinical and Phase 1 Results), the effect of deuterium incorporation on the metabolic fate of each enantiomer of methadone must be determined.

The transporter P-glycoprotein (P-gp, ABCB1) limits the delivery of the clinically used racemic methadone across the blood-brain barrier (BBB) because both R- and S-enantiomers of methadone are substrates of P-gp (Wang et al., *Psychopharmacology* (*Berl*). 173(1-2):132-8, 2004). Furthermore, P-gp exhibits different stereoselectivity towards the R- and S-enantiomers of methadone, as evident from the different ratios of (R)- and (S)-methadone in the brain of $Abcb1a^{-/-}$ mice vs $Abcb1a^{+/+}$ mice (15.3 vs. 23.5) (Wang et al., *Psychopharmacology* (*Berl*). 173(1-2):132-8, 2004). From these data, the authors concluded that "the polymorphic expression of P-gp in humans may represent a source of inter-individual variation of methadone access to the central nervous system" (Wang et al., *Psychopharmacology*

(*Berl*). 173(1-2):132-8, 2004). To the best of the Inventors' knowledge, there are no reports describing how deuterium incorporation affects the permeability of drugs across cells expressing P-gp.

Effect of deuteration on the pharmacokinetic profile of $d_9$-methadone and acute toxicity Previously, Elison et al. reported that the substitution of deuterium for hydrogen in the N—$CH_3$ group of morphine resulted in a reduction in the rate of oxidative N-demethylation of $d_3$-morphine compared to nondeuterated morphine (Elison et al., *Science.* 134 (3485):1078-9, 1961). On the other hand, Hsia et al. showed that trideuteriomethadone ($d_3$-methadone) had similar analgesic activity and toxicity in mice as methadone (Hsia et al., *Science.* 193(4252):498-500, 1976). Furthermore, the rates of absorption, distribution, and excretion of $d_3$-methadone and methadone in rats were also identical, suggesting that the replacement of the hydrogen atoms at C-1 with deuterium atoms did not affect its pharmacokinetic and pharmacodynamic properties(Hsia et al., *Science.* 193(4252):498-500, 1976).

Figure 4:
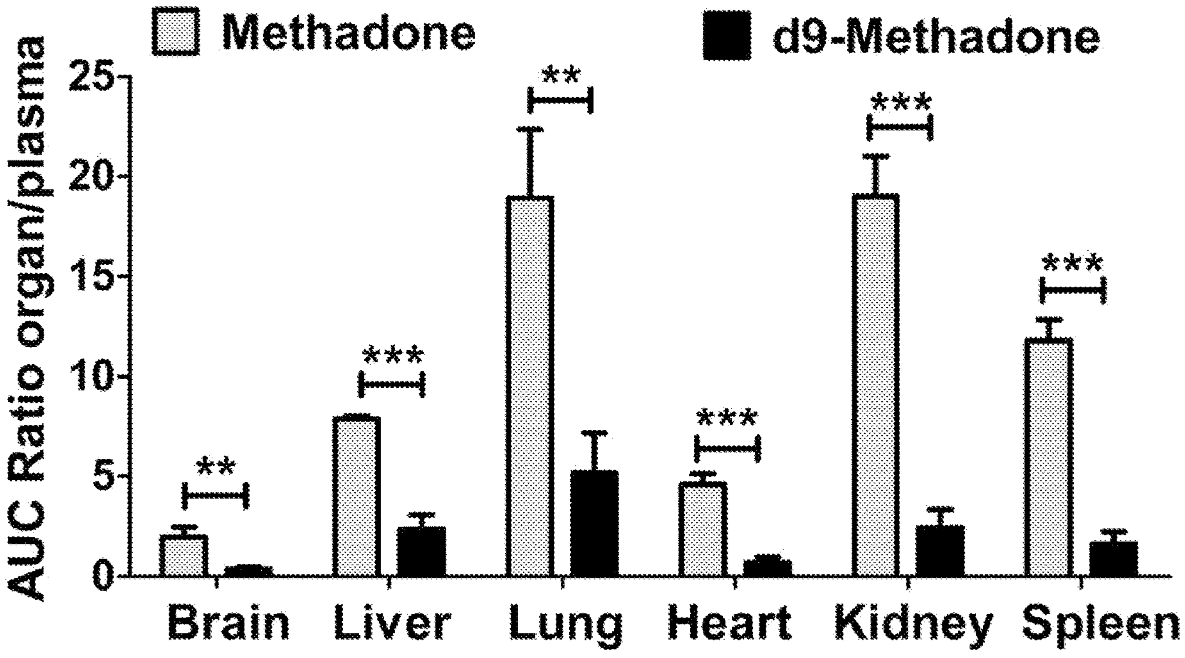
FIG. 4. Ratio of $AUC_{0-8h}$ of methadone or $d_9$-methadone in different organs to the $AUC_{0-8h}$ in plasma. Each mouse was administered 2 mg/kg of $d_9$-methadone or methadone intravenously via the tail vein. At predetermined time points (5 min, 15 min, 30 min, 1 h, 2 h, 3 h, 4 h, 6 h, and 8 h), n=1 animal per time point was sacrificed by $CO_2$ asphyxiation, and the tissue samples were collected. The quantification of methadone and $d_9$-methadone in tissue samples was performed using an LC-MS/MS method. AUC values for methadone and $d_9$-methadone in each organ were determined using Kinetica software (v. 5.1). Data are presented as the mean+s.d. of 3 separate experiments using 1 animal per time point. N=3 animals were used for each time point. AUC, area under the concentration vs. time curve. P<0.01; *P<0.001.

However, data obtained in the Inventors' laboratory show that the apparent Vmax of the formation of $d_6$-EDDP from $d_9$-methadone by mouse liver microsomes (MLM) was 2.5-fold lower than the $V_{max}$ of the formation of EDDP from methadone. Meanwhile, the apparent Km of $d_9$-methadone was 2.6-fold lower than the Km of methadone. Similar results were obtained using human liver microsomes (HLM): the estimated apparent Km and Vmax values for methadone N-demethylation were 2- and 2.5-folds lower than the corresponding values estimated for $d_9$-methadone N-demethylation. The replacement of three hydrogen atoms in three methyl groups of methadone also affected its PK properties. The AUC0-$_8$h and Cmax of $d_9$-methadone were greater than the AUC0-$_8$h and Cmax of methadone, and the clearance of $d_9$-methadone was lower than that of methadone (Table 2). The decreased Vss for $d_9$-methadone suggested that this deuterated analog of methadone remains mainly in the plasma, which is in agreement with its increased Cmax and AUC0-$_8$h values in the plasma. Furthermore, the AUC0-$_8$h value determined for the metabolite, $d_6$-EDDP, demonstrated that deuteration of methadone also decreased the formation of $d_6$-EDDP and consequently resulted in a decreased metabolite-to-parent drug ratio. The PK study also revealed that the levels of $d_9$-methadone and methadone in the brain were similar; however, the brain-to-plasma ratio for $d_9$-methadone was 5.8-fold lower than the brain-to-plasma ratio of methadone. Similar to the brain-to-plasma AUC ratio, the organ-to-plasma AUC ratios in the liver, lung, heart, kidney, and spleen for $d_9$-methadone were also reduced several fold as compared to those of methadone (FIG. 4). These data indicate that the replacement of 3 hydrogen atoms in 3 methyl groups of methadone altered pharmacokinetic properties of methadone. Moreover, the estimated $LD_{50}$ value for a single intravenous dose of $d_9$-methadone was 2.1-fold higher than the estimated LD50 value for a single i.v. dose of methadone.

Effect of deuteration on the analgetic efficacy of methadone. The efficacy of deuterated compounds due to deuterium switch can be equivalent to the non-deuterated analogue (Harbeson and Tung, *Medchem News.* 24(2):8-22, 2014) or even enhanced (Concert Pharmaceuticals presents positive 48-week results from Phase 2 clinical trail of CTP-499 in diabetic kidney disease. 2014). For example, in 2016, a U.S. Pat. No. 9,447,108 was granted for new deuterated morphine derivatives which showed higher affinity to μ-opioid receptors and produced longer antinociception effects as compared to morphine. Deuterated methadone may have greater therapeutic effects on pain than nondeuterated methadone. This notion has a clinical significance particularly in this era of public health crisis caused by increased prescription of opioid analgesics including methadone (*MMWR Morb Mortal Wkly Rep.* 61(26):493-7, 2012). If deuteration increases the analgesic efficacy of methadone while decreasing its metabolic unpredictability and toxicity, deuterated methadone will be a feasible, direct countermeasure to the crisis. Recent studies have reported the superiority of methadone over morphine for the treatment of postoperative pain with either intra- or post-operative treatment regimen (Kharasch, *Anesth Analg.* 112(1):13-6, 2011; Gottschalk et al., *Anesth Analg.* 112(1):218-23, 2011; Neto et al., *J Anesth.* 28(4):505-10, 2014), which prompts a preclinical investigation into the therapeutic potential of deuterated methadone for postoperative pain management.

Effect of deuteration on the abuse liability of methadone. Methadone does not have euphoric effects as strong as other widely used opioid analgesics reportedly because of its low potency at the μ-opioid receptor and galanin receptor-1 heteromers that ultimately activate dopaminergic reward system in the brain (Cai et al., *J Clin Invest.* 129(7):2730-2744, 2019). In this regard, it is an important question whether deuteration would alter such a beneficial property of methadone in terms of the reward system activation. To address this question, the inventors tested whether mice that received $d_9$-methadone would develop preference for the drug-paired chamber in a conditioned place preference (CPP) behavioral paradigm. In contrast to mice treated with morphine (an analgesic with strong abuse liability), mice treated with nondeuterated methadone showed relatively weaker conditioned place preference, which aligns with its weaker euphoric effect than that of morphine. Mice treated with $d_9$-methadone did not show any apparent conditioned place preference (FIG. 8), indicating that the deuteration further decreased the abuse liability of methadone.

The data presented in this application indicates that substitution of deuterium for hydrogen in 3 methyl groups of methadone altered the pharmacokinetic properties of methadone, improved its safety, and enhanced its analgesic effect in mice. The data indicate that it is reasonable to expect increased area under the time-concentration curve (AUC), and reduced clearance of $d_9$-methadone. The data also suggest that deuteration may enhance metabolic stability of methadone which could lead to decreased interindividual variabilities in plasma concentrations of methadone.

With respect to safety, $d_9$-methadone has lower toxicity potential than methadone. This observation, together with the PK changes of increased AUC and reduced clearance of the drug could promote the use of lower doses of $d_9$-methadone and/or decreased frequencies of $d_9$-methadone administration. These changes will lead to reduced side effects and decrease the risks for fatal and non-fatal overdoses.

With respect to the analgesic efficacy and abuse liability, data suggest that $d_9$-methadone outperforms its nondeuterated isotope, which has an immediate clinical relevance and significance because $d_9$-methadone is a feasible countermeasure to the current opioid crisis as an improved version of opioid analgesic.

Thus, embodiments described herein are directed to $d_9$-methadone as an alternative formulation of methadone—with an improved absorption-distribution-metabolism-excretion profile, analgetic efficacy, and safety—for the management of postoperative pain.

As described herein, $d_9$-methadone has a lower affinity for human hepatic microsomal metabolizing enzymes as compared to the affinity of nondeuterated methadone. Moreover, the metabolite/parent compound ratios ($d_6$-EDDP/$d_9$-methadone) in both mouse plasma and liver were lower than the corresponding ratios of EDDP/methadone. Also, data suggest that following intravenous administration, the acute toxicity of $d_9$-methadone in mice (LD50 24.8 mg/kg) is less than that of methadone (LD50 11.6 mg/kg). In addition, $d_9$-methadone outperformed its nondeuterated counterpart in the efficacy against postoperative pain and the assessment of abuse risk in animal models.

II. $d_9$-METHADONE THERAPIES

Compositions comprising $d_9$-methadone as described herein can be used in combination with or as a substitute for methadone. Methadone is an important long-term maintenance therapy for drug addiction that is very frequently employed in clinical practice. Additionally, methadone is used as an analgesic therapy. The composition includes therapeutically effective amounts of $d_9$-methadone. In one embodiment, $d_9$-methadone is present in a dosage of at least about 0.5 mg. In another embodiment, it is present in a range from about 2 mg to about 300 mg per dose. The dosage generally depends upon the targeted subject and the particular formulation. For example, amounts in the range from about 2 mg to about 6 mg are generally suitable in children while higher amounts, such as in the range from about 6 mg to about 300 mg, are generally suitable for adults. In certain embodiments, administration of $d_9$-methadone is in an amount between 5 mg and 300 mg. In some embodiments, the dose of $d_9$-methadone is 0.1, 0.5, 1, 5, 10, 20, 25, 30, 40, 50, 60, 70, 75, 80, 90, 100, 110, 120, 130, 140, 15, 200, 250, to 300 mg (including all values and ranges there between). Preferably, the unit dose is between 20 mg and 120 mg per subject per day.

The subject may also receive $d_9$-methadone in the range of about 0.1, 0.5, 1.0, 5.0, 10, 50, 100, to 300 mg per dose one or more times per day, week, or month (e.g., 2, 3, 4, 5, 6, or 7 or more times per day, week, or month).

Pain Management

Opioid analgesics, one of the widely used abuse-prone drugs, are a mainstay of pain management. For example, they may be used to manage pain due to traumatic injury or surgery, pain produced by chronic inflammatory conditions such as osteoarthritis, rheumatoid arthritis and lower back pain. They may also be used to treat pain due to mixed nociceptive/neuropathic etiologies, such as cancer or fibromyalgia. Opioids may also be used to manage neuropathic pain, including pain associated with diabetic neuropathy, postherpetic neuralgia, HIV/AIDS, traumatic injury to nerves, complex regional pain syndrome type II, trigeminal neuralgia, erythromelalgia and phantom pain.

Pain that is treated may be any type of pain, including neuropathic pain, which is for example caused by damage or disease that affects the somatosensory nervous system. Pain that is treated may be nociceptive pain, such as for example that is caused by tissue damage or injury, including for example surgical incision or resection, broken bones and cuts or scrapes. Pain that is treated may be nociplastic pain, such as for example that arises from altered nociception despite no clear evidence of actual or threatened tissue damage, including for example complex regional pain syndrome type I. Pain may also be mixed such that it includes neuropathic, nociceptive, and nociplastic pain. In a preferred embodiment, pain that is treated is neuropathic. In another preferred embodiment, pain that is treated is mixed.

Pain treated by administration of the compositions of the present invention may be acute or chronic. In a preferred embodiment, pain that is treated is chronic. In another preferred embodiment, pain that is treated is chronic, neuropathic pain.

Neuropathic pain may be found in conditions such as for example without limitation back pain, neck pain, spinal cord injury, phantom limb pain, carpal tunnel syndrome, multiple sclerosis, stroke, chemotherapy-induced neuropathy, diabetic neuropathy and other metabolic conditions, herpes zoster infection, HIV-related neuropathies, nutritional deficiencies, toxins, immune-mediated disorders, physical trauma to a nerve trunk, mononeuropathy, polyneuropathy, nerve entrapment, cancer, chemotherapy, radiation injury, surgery, radiculopathy and scar pain.

Nociceptive pain may be found in conditions such as for example without limitation post-operations, sprains, bone fractures, degenerative disease of discs and joints, back pain, neck pain, burns, bumps, bruises, inflammation for example from infection or arthritis, obstructions and myofascial pain.

Nociplastic pain may be found in conditions such as for example without limitation post-operations beyond the normal recovery time, post-trauma beyond the normal healing time, post-infections beyond the normal resolution time, and visceral pain without detectable organic abnormalities.

In an embodiment of mixed pain, acute painful conditions, often associated with nociceptive pain, may transition to chronic neuropathic or nociplastic pain in a subject. Alternatively, a subject may have mixed pain including one or more condition associated with neuropathic pain, one or more condition associate with nociceptive pain, and one or more condition associate with nociplastic pain. A subject with mixed pain may have back pain, neck pain, or both back pain and neck pain with neuropathic and nociceptive components. For example, without limitation, mixed pain may include back pain, neck pain, or both after surgery, e.g., postlaminectomy syndrome.

The present invention includes methods for treatment of pain, wherein pain in the subject is reduced or eliminated as compared with pain before treatment of the subject by administration of a composition comprising $d_9$-methadone. Reduction of pain includes a reduction in pain by any amount and may be measured by any means conventionally used by the skilled artisan to evaluate pain in a subject. Elimination of pain in a subject means that no pain is detected in a subject as measured by conventional means or no pain is reported by the subject.

Effective treatment of pain in a subject may include any reduction of pain, including for example decreased burning, pricking, tingling, aching, throbbing, stinging, soreness or any combination thereof in the subject.

Methods of treatment of pain provided herein may include measuring reduction of pain by any conventional means known to the skilled artisan. For example, in some rodents, a tail flick study may be used to assess pain before and after administration of a mixture or composition of the invention. In an embodiment, for a human subject self-reporting may be used to identify decreased pain. Alternatively, functional magnetic resonance imaging (fMRI) may be used in a subject to identify decreased pain following administration of a mixture or composition of the present invention.

In accordance with the methods of the present invention, reduction or elimination of pain in a subject may last for any amount of time. For example, reduction or elimination of pain may last for about 1 hour, about 2 hours, about 3 hours, about 4 hours, about 5 hours, about 6 hours, about 7 hours, about 8 hours, about 10 hours, about 12 hours, about 14 hours, about 16 hours, about 20 hours, or about 24 hours. In other preferred embodiments reduction or elimination of pain in a subject may last for about 2 days, about 3 days, about 4 days, about 5 days, about 6 days, or about 7 days. In further preferred embodiments, reduction or elimination of pain in a subject may last for about 2 weeks, about 3 weeks, about a month, about 2 months, about 3 months, about 4 months, about 5 months, about 6 months, about 1 year, or for as long as the mixtures or compositions or the present invention continue to be administered. It is also contemplated that the compositions of the present invention may be administered in an extended release formulation, such as a formulation that is suitable for dosing, for example without limitation, once a week, once every two weeks, or once a month.

Drug Addiction

Opiates are narcotic agonistic analgesics and are drugs derived from opium, such as morphine, codeine, and many synthetic congeners of morphine, with morphine being the most widely used derivative. Opioids are natural and synthetic drugs with morphine-like actions and include the opiates. Opioids are narcotic agonistic analgesics which produce drug dependence of the morphine type and are subject to control under federal narcotics law because of their addicting properties.

The chemical classes of opioids with morphine-like activity are the purified alkaloids of opium consisting of phenanthrenes and benzylisoquinolines, semi-synthetic derivatives of morphine, phenylpiperidine derivatives, morphinan derivatives, benzomorphan derivatives, diphenylheptane derivatives, and propionanilide derivatives. The principal phenanthrenes are morphine, codeine, and thebaine. The principal benzoisoquinolines are papaverine, a smooth muscle relaxant, and noscapine. Semi-synthetic derivatives of morphine include diacetylmorphine (heroin), hydromorphone, oxymorphone, hydrocodone, apomorphine, etorpine, and oxycodone. Phenylpiperidine derivatives include meperidine and its congeners diphenoxylate and loperamide, alphaprodine, anileridine hydrochloride or phosphate, and piminodine esylate. Morphinan derivatives include levorphanol. The diphenyl-heptane derivatives include methadone and its congeners, and propoxyphene. Propionanilide derivatives include fentanyl citrate and its congeners sufenil citrate and alfenatil hydrochloride. These opioid analgesics are discussed in detail in Goodman and Gilman's The Pharmacological Basis of Therapeutics, Chapter 21, "Opioid Analgesics and Antagonists", pp. 485-521 (8th ed. 1990), which is incorporated herein by reference.

In addition to the analgesic solution of the present invention, the present invention also provides a solution for use in the treatment of a subject's drug addiction to narcotic drugs comprising a therapeutically effective amount of $d_9$-methadone.

A subject who should withdraw from a narcotic drug or is undergoing withdrawal from a narcotic drug may be treated by administering to the individual a therapeutically effective amount of the $d_9$-methadone composition. Administration enables the individual to withdraw from the narcotic drug and eliminate dependency on the narcotic drug without the drug withdrawal symptoms and the pain associated with those symptoms.

In certain embodiments, the subject has an addiction. In certain embodiments, the addiction is a drug addiction, for example, an opiate addiction. In certain aspects, the invention provides a method for treating an addiction comprising administering to a subject in need thereof a therapeutically effective amount of $d_9$-methadone.

III. PHARMACEUTICAL FORMULATIONS

In light of the current specification, the determination of an appropriate treatment regimen (e.g., dosage, frequency of administration, systemic vs. local, etc.) is within the skill of the art. For administration, the components described herein will be formulated in a unit dosage form (solution, suspension, emulsion, etc.) in association with a pharmaceutically acceptable carrier. Such vehicles are usually nontoxic and non-therapeutic. Examples of such vehicles are water, saline, Ringer's solution, dextrose solution, and Hank's solution. Non-aqueous vehicles such as fixed oils and ethyl oleate may also be used. A preferred vehicle is 5% (w/w) human albumin in saline. The vehicle may contain minor amounts of additives, such as substances that enhance isotonicity and chemical stability, e.g., buffers and preservatives.

The therapeutic compositions described herein, as well as their biological equivalents, can be administered independently or in combination by any suitable route. Examples of parenteral administration include intravenous, intraarterial, intramuscular, intraperitoneal, and the like. The routes of administration described herein are merely an example and in no way limiting.

The dose of the therapeutic compositions administered to an animal, particularly in a human, in accordance with embodiments of the invention, should be sufficient to result in a desired response in the subject over a reasonable time frame. It is known that the dosage of therapeutic compositions depends upon a variety of factors, including the strength of the particular therapeutic composition employed, the age, species, condition or disease state, and the body weight of the animal.

Moreover, dose and dosage regimen, will depend mainly on the type of biological damage to the host, the type of subject, the history of the subject, and the type of therapeutic composition being administered. The size of the dose will be determined by the route, timing and frequency of administration as well as the existence, nature and extent of any adverse side effects that might accompany the administration of a particular therapeutic composition and the desired physiological effect. It is also known that various conditions or disease states, in particular, chronic conditions or disease states, may require prolonged treatment involving multiple administrations.

Therefore, the amount of the therapeutic composition must be effective to achieve an enhanced therapeutic index. If multiple doses are employed, the frequency of administration will depend, for example, on the type of subject. One skilled in the art can ascertain upon routine experimentation the appropriate route and frequency of administration in a given subject that are most effective in any particular case. Suitable doses and dosage regimens can be determined by conventionally known range-finding techniques. Generally, treatment is initiated with smaller dosages, which are less than the optimal dose of the compound. Thereafter, the dosage is increased by small increments until the optimal effect under the circumstances is obtained.

The therapeutic compositions for use in embodiments of the invention generally include carriers. These carriers may be any of those conventionally used and are limited only by the route of administration and chemical and physical considerations, such as solubility and reactivity with the therapeutic agent. In addition, the therapeutic composition may be formulated as polymeric compositions, inclusion complexes, such as cyclodextrin inclusion complexes, liposomes, microspheres, microcapsules, vesicle preparation from human cells and tissues and the like, without limitation.

The pharmaceutically acceptable excipients described herein, for example, vehicles, adjuvants, carriers, or diluents, are well known and readily available. It is preferred that the pharmaceutically acceptable carrier be one which is chemically inert with respect to the therapeutic composition and one that has no detrimental side effects or toxicity under the conditions of use.

The choice of excipient will be determined, in part, by the particular therapeutic composition, as well as by the particular method used to administer the composition. Accordingly, there are a wide variety of suitable formulations of the pharmaceutical composition used in the embodiments of the invention. For example, the non-limiting formulations can be injectable formulations such as, but not limited to, those for intravenous, subcutaneous, intramuscular, intraperitoneal injection, and the like, and oral formulations such as, but not limited to, liquid solutions, including suspensions and emulsions, capsules, sachets, tablets, lozenges, and the like. Non-limiting formulations suitable for parenteral administration include aqueous and non-aqueous isotonic sterile injection solutions, including non-active ingredients such as antioxidants, buffers, bacteriostats, solubilizers, thickening agents, stabilizers, preservatives, surfactants, and the like. The solutions can include oils, fatty acids, including detergents and the like, as well as other well-known and common ingredients in such compositions, without limitation.

IV. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Deuterated Methadone

The following studies are designed to determine:

(i) The effect of the replacement of three hydrogen atoms in three methyl groups on the biotransformation of methadone (1A) and its interactions with P-gp (1B). (a) The stereo-selective metabolism of racemic $d_9$-methadone will be determined using human liver microsomes and microsomes expressing CYP2B6, 2D6, 2C9, 2C19, 3A4, and 3A5 and compared to the stereo-selective metabolism of racemic methadone. (b) The extent to which P-gp mediates the efflux of $d_9$-methadone in comparison to nondeuterated methadone will be determined using the human brain microvascular endothelial cell line hCMEC/D3.

(ii) Determine the pharmacokinetic profile as well as the acute toxicity of $d_9$-methadone. (a) Pharmacokinetic and tissue distribution studies of R- and S-enantiomers of $d_9$-methadone will be determined in male and female C57BL/6 mice following intravenous and oral administration and will be compared to that of racemic nondeuterated methadone. (b) Oral and intravenous single-dose toxicities of $d_9$-methadone will be tested using the up-and-down (UDP) method in female and male C57BL/6 mice and compared to that of racemic nondeuterated methadone.

(iii) Determine the analgesic efficacy and abuse liability of $d_9$-methadone. (a) In naïve mice, we will determine the efficacy of $d_9$-methadone against acute mechanical and thermal pain by measuring nocifensive withdrawals as the behavioral readout of the sensory-discriminative domain of pain. (b) In the moue model of plantar incision, the efficacy of $d_9$-methadone against postoperative pain will be determined using both intraoperative and postoperative treatment regimens. We will also determine the effects of $d_9$-methadone on the affective-motivational domain of pain, using a conflict avoidance behavioral paradigm. (c) In naïve mice, we will determine whether $d_9$-methadone poses a risk of abuse in a conditioned place preference paradigm.

N-demethylation of Methadone, $d_3$-Methadone, and $d_9$-Methadone.

The activity of human hepatic microsomes in catalyzing the N-demethylation of methadone to EDDP, $d_3$-methadone to $d_3$-EDDP, and $d_9$-methadone to $d_6$-EDDP was determined.

The reaction components contained 100 mM potassium phosphate buffer, pH=7.4, 0.1 mg of pooled human liver microsomes, and 50 μM, 100 μM, and 200 μM of methadone, $d_3$-methadone, or $d_9$-methadone in a total volume of 0.2 mL. The reaction mixture was preincubated for 5 minutes at 37° C. and the reaction was initiated by the addition of an NADPH-regenerating system made of the following: 0.08 mM NADP, 0.8 mM glucose-6-phosphate, 0.2 U/mL glucose-6-phosphate dehydrogenase, and 0.4 mM $MgCl_2$. The reaction was incubated for 20 min at 37° C. and terminated by the addition of 1.2 mL of cold acetonitrile.

Analytical method: An LC-MS/MS method for the quantification of EDDP, $d_3$-EDDP and $d_6$-EDDP was developed and validated. The samples were analyzed with an API 4000 triple quadrupole mass spectrometer coupled with an Agilent HPLC 1200 system (Applied Biosystems, Foster City, CA). The system was controlled by Analyst™1.5 Software (MDS INC. and Applera Corporation, USA). Separation of EDDP, $d_3$-EDDP and $d_6$-EDDP was achieved by a Waters Symmetry $C_{18}$ HPLC column at 45° C. The mobile phase was made of (A) acetonitrile and (B) 0.1% formic acid aqueous solution (v/v) with gradient elution of 0-3 min, 27% A to 45% A with flow rate at 350 μL/min. Before each injection, the HPLC column was equilibrated with 27% A for 6 min. Multiple reaction monitoring (MRM) was set up at m/z 278→249 for EDDP, m/z 281→249 for $d_3$-EDDP, and 284→249 for $d_6$-EDDP. The $d_3$-EDDP was used as a surrogate standard for quantification of $d_6$-EDDP due to the unavailability of EDDP standard on the market.

Data indicate that the formation of EDDP, $d_3$-EDDP, and $d_6$-EDDP was dependent on substrate concentration (FIG. 1). As compared to the non-deuterated substrate, deuteration of methadone significantly decreased the biotransformation of the tested deuterated compounds. Furthermore, as compared to $d_3$-methadone, replacement of 3 hydrogen atoms with deuterium in 3 methyl groups of methadone further decreased the rate of $d_9$-methadone metabolism in vitro. The data are presented as mean±standard deviation. Each reaction was performed in duplicate and repeated two times.

Metabolism of methadone and $d_9$-methadone in vitro. The activity of mouse liver microsomes (MLM) and human liver microsomes (HLM) in catalyzing the N-demethylation of methadone to EDDP and $d_9$-methadone to $d_6$-EDDP was determined following the protocol described previously (Fokina et al., *Am J Perinatol* 28(1):25-32, 2011). The stock solutions of methadone and $d_9$-methadone were prepared as described above for the PK study, except that potassium phosphate buffer was used instead of PBS. Methadone and $d_9$-methadone were used in a range of concentrations to construct saturation curves for the formation of their corresponding metabolites as follows: methadone, 7.5-100 μM with MLM and 15-300 μM with HLM; and $d_9$-methadone, 1.875-60 μM with MLM and 7.5-100 μM with HLM. N=3 experiments were conducted for each drug, with each point in triplicate. Each reaction mixture (total volume of 0.2 mL in 100 mM potassium phosphate buffer, pH 7.4) containing 0.025 mg of pooled HLM (XenoTech, LLC, Kansas City, KS) or 0.05 mg of pooled MLM from male CD-1 mice (XenoTech, LLC, Kansas City, KS) and either methadone or $d_9$-methadone was pre-incubated for 5 minutes at 37° C. The reaction was initiated by the addition of NADPH-regenerating system (0.4 mM NADP; 4 mM glucose-6-phosphate; 1 U/mL glucose-6-phosphate dehydrogenase and 2 mM $MgCl_2$) and carried out at 37° C. The duration of the reaction was 10 minutes for MLM and 20 minutes for HLM. The reaction was terminated by placement of the tubes on ice and the addition of 20 μL of $Li_2CO_3$ (10 mg/mL working solution) and 1.2 mL of ice-cold acetonitrile containing 1% formic acid to each tube as well as the respective internal standard. The samples were processed as described above; the final residues were reconstituted with 200 μL of the initial mobile phase and analyzed by means of LC-MS/MS for the quantitative determination of either EDDP or $d_6$-EDDP as described above. For each concentration of methadone and $d_9$-methadone, the control reactions were conducted in the absence of NADPH-regenerating system, and the background quantities of EDDP and $d_6$-EDDP were subtracted from the respective EDDP and $d_6$-EDDP quantities determined in the reactions with NADPH. To minimize the number of freeze/thaw cycles of the liver microsomal proteins, the pooled microsomes were aliquoted and stored at −80° C. as recommended by the manufacturer, and individual aliquots were defrosted for each experiment. The mouse and human liver microsomes utilized in this work were from the same respective lots to eliminate the influence of potential donor-associated variability in the activity of the hepatic enzymes. The experimental conditions were optimized using 30 μM of methadone for the MLM and HLM protein amounts and incubation time to assure that the formation of EDDP was within the linear range (assuming that the formation of $d_6$-EDDP from $d_9$-methadone was also linear under the same experimental conditions). The apparent Michaelis constant ($K_m$) and maximum velocity ($V_{max}$) values were estimated using SigmaPlot software, version 14.5.0.101 (Systat Software, Inc., Palo Alto, CA) using pooled data from n=3 saturation curves for each of the substrates. The intrinsic metabolic clearance $CL_{int}$ was calculated as $V_{max}/K_m$ (Sharma et al., *Drug Metab Dispos* 40(3):625-34, 2012); and the deuterium effect on the reaction was evaluated based on a ratio of $V_{max}$ and $CL_{int}$ parameters for the non-deuterated substrate to those of the deuterated substrate.

Figure 2A:
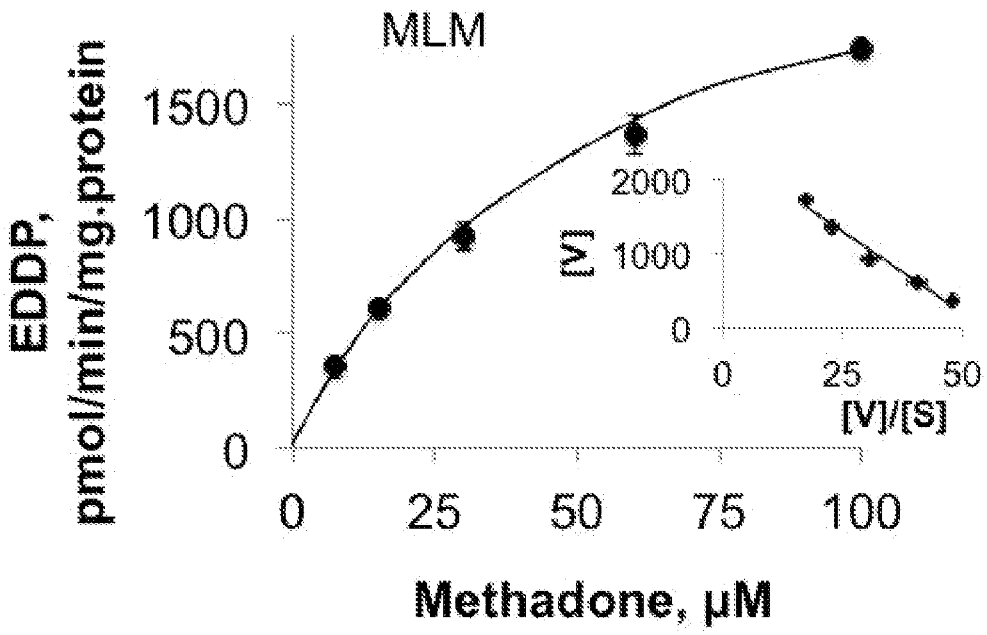
FIG. 2A-2B. N-demethylation of methadone and $d_9$-methadone into their respective metabolites, EDDP (A) and $d_6$-EDDP (B) in vitro. N-demethylation of methadone and $d_9$-methadone into their respective metabolites, EDDP and $d_6$-EDDP were tested in vitro using mouse liver microsomes (MLM) (A and B, respectively) and human liver microsomes (HLM) (not shown). The substrates were used in the following ranges: methadone, 7.5-100 μM with MLM and 15-300 μM with HLM; and $d_9$-methadone, 1.875-60 μM with MLM and 7.5-100 μM with HLM. The substrates were incubated with the microsomal proteins at pH 7.4 in the presence of NADPH and in the absence of the cofactor (control reactions) at 37° C. for either 10 min (MLM) or 20 min (HLM). The CYP-catalyzed formation of EDDP and $d_6$-EDDP was calculated by subtracting the metabolite quantities determined in the control reactions from those determined in the reactions with NADPH. The rates of the formation of EDDP and $d_6$-EDDP were dependent on the substrate concentrations and were fitted into the Michaelis-Menten model using SigmaPlot (version 14.5.0.101 for Windows, Systat Software Inc.). The insets show the corresponding Eadie-Hofstee plots. Data are presented as the mean±s.d. from n=3 experiments, with each point in triplicate. The estimated kinetic parameters of the reactions are shown in Table 2. [V], reaction velocity, pmol/min/mg·protein; [S], substrate concentration, μM; EDDP, 2-ethylidene-1,5-dimethyl-3,3,-diphenylpyrrolidine; MLM, mouse liver microsomes; HLM, human liver microsomes.
Figure 2B:
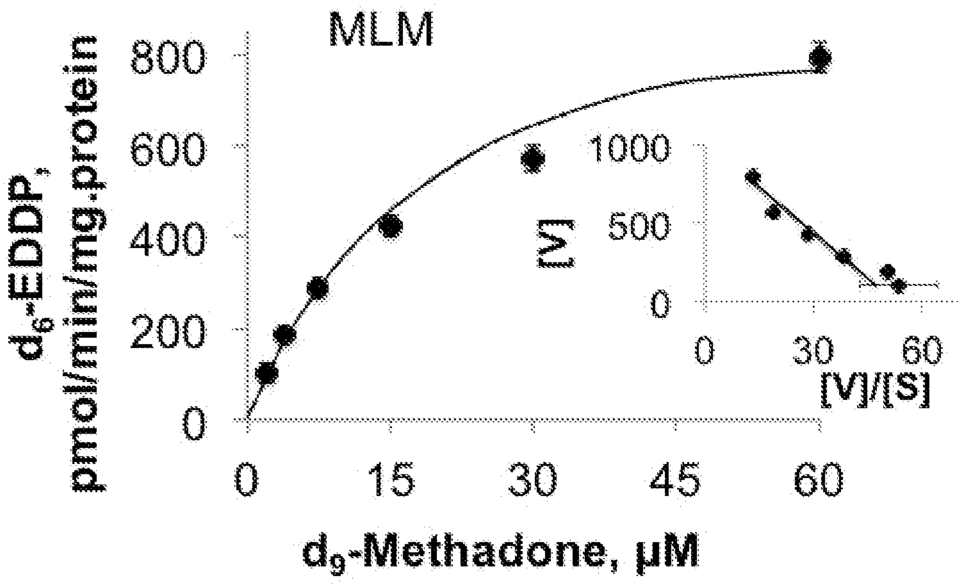
Figures 3A, 3B:
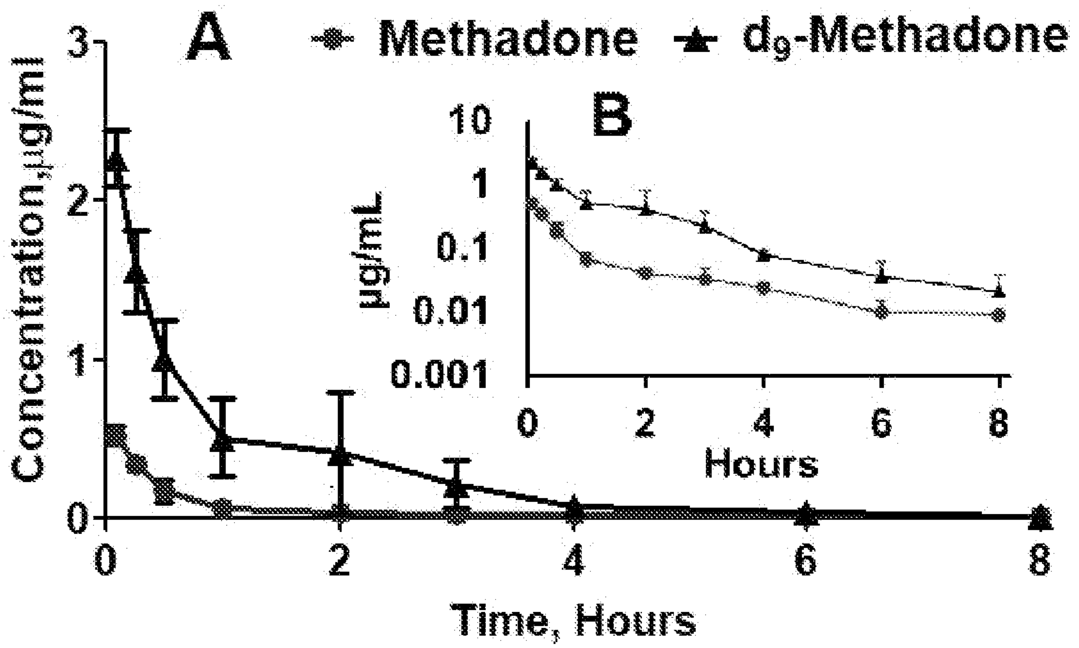
FIG. 3A-3D. Plasma concentration-time profiles for methadone and $d_9$-methadone on a linear scale (A) and logarithmic scale (B) and their metabolites EDDP and $d_6$-EDDP on a linear scale (C) and logarithmic scale (D) after intravenous administration to male CD-1 mice. Each mouse was administered 2 mg/kg of $d_9$-methadone or methadone intravenously via the tail vein. At the predetermined time points of 5 min, 15 min, 30 min, 1 h, 2 h, 3 h, 4 h, 6 h, and 8 h, animals were sacrificed by $CO_2$ asphyxiation and blood samples were obtained by cardiac puncture. The quantification of methadone, $d_9$-methadone, EDDP and $d_6$-EDDP in plasma samples was performed using an LC-MS/MS method. Data are presented as the mean±s.d. of 3 separate experiments using 1 animal per time point. N=3 animals were used for each time point. EDDP, 2-ethylidene-1,5-dimethyl-3,3,-diphenylpyrrolidine.
Figures 3C, 3D:
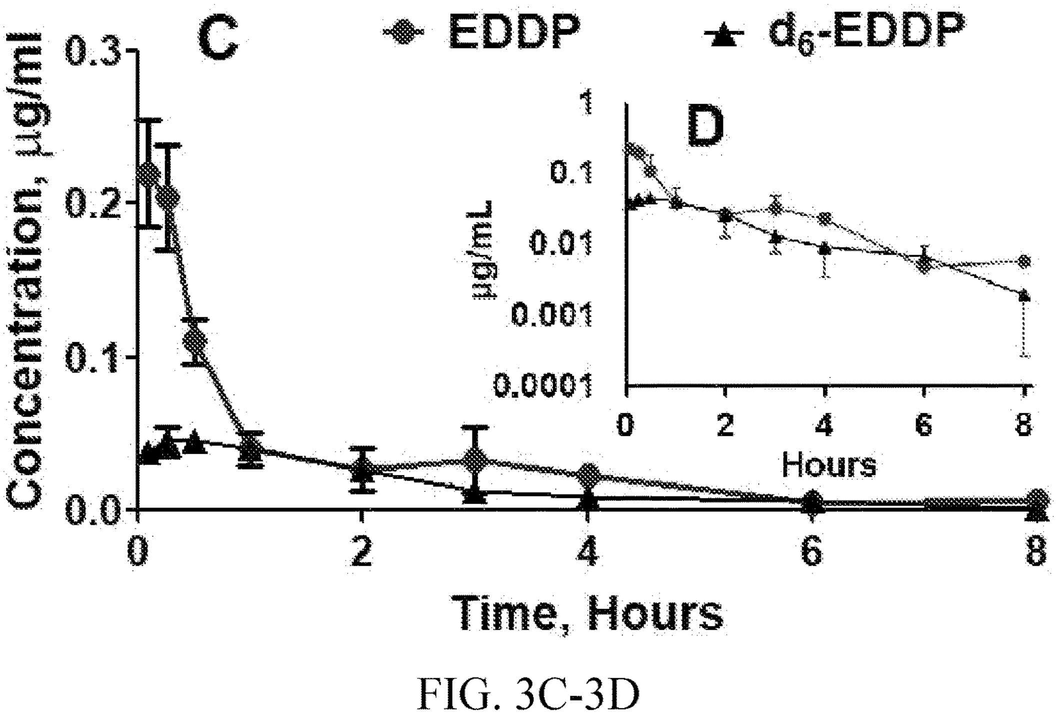

Data indicate that the rates of the formation of EDDP and $d_6$-EDDP from methadone and $d_9$-methadone, respectively, were dependent on the substrate concentrations and exhibited typical saturation kinetics (FIG. 2A-2B). The apparent $K_m$ and $V_{max}$ values are shown in Table 1. The apparent $V_{max}$ of the formation of $d_6$-EDDP from $d_9$-methadone by MLM was 2.5-fold lower than the $V_{max}$ of the formation of EDDP from methadone. Meanwhile, the apparent $K_m$ of $d_9$-methadone was 2.6-fold lower than the $K_m$ of methadone. Similar results were obtained using HLM: the estimated apparent $K_m$ and $V_{max}$ values for methadone N-demethylation were 2- and 2.5-folds lower than the corresponding values estimated for $d_9$-methadone N-demethylation (Table 4). Thus, the deuteration effects of the drug's N-demethylation $V_{max}$ ($^{H}V_{max}/^{D}V_{max}$) and $CL_{int}$ ($^{H}CL_{int}/^{D}CL_{int}$) were 2.5 and 1.3, respectively, in MLM, and 2.5 and 1, respectively, in HLM, and were deemed as isotope effects of low magnitude (<3.6) according to Miwa and Walsh (Miwa et al., *J Biol Chem* 258(23):14445-9, 1983).

TABLE 1

Kinetic parameters of the formation of EDDP and $d_6$-EDDP from methadone and $d_9$-methadone, respectively, by mouse and human liver microsomes.

| Subcellular fraction | Substrate | $K_m$ (μM) Best fit value | 95% CI | $V_{max}$ (pmol · min$^{-1}$ · mg of protein$^{-1}$) Best fit value | 95% CI | $CL_{int}$ ($V_{max}/K_m$) |
|---|---|---|---|---|---|---|
| MLM | Methadone | 53.5 ± 5.1 | (42.3, 64.6) | 2631 ± 121 | (2368, 2893) | 49.2 |
| | $d_9$-Methadone | 20.7 ± 2.1 | (16.2, 25.2) | 1033 ± 45 | (937, 1129) | 49.7 |
| HLM | Methadone | 82.9 ± 3.7 | (74.7, 91.0) | 1116 ± 17 | (1080, 1152) | 13.5 |
| | $d_9$-Methadone | 41.3 ± 5.9 | (28.4, 54.1) | 438 ± 27 | (379, 497) | 10.6 |

The effect of the range of methadone and $d_9$-methadone concentrations on the respective formation of EDDP and $d_6$-EDDP was examined in mouse liver microsomes (MLM) and human liver microsomes (HLM) (FIG. 10). The kinetic parameters were estimated by fitting the data in the Michaelis-Menten model using SigmaPlot software (version 14.5.0.101, Systat Software Inc., Palo Alto, CA).

Data are presented as the mean ± S.E. of n = 3 experiments.

EDDP, 2-ethylidene-1,5-dimethyl-3,3,-diphenylpyrrolidine;

HLM, human liver microsomes;

MLM, mouse liver microsomes;

$K_m$, Michaelis constant;

$V_{max}$, maximum velocity;

CI, confidence interval;

$CL_{int}$, intrinsic metabolic clearance.

Determine Effect of the Replacement of Three Hydrogen Atoms in Three Methyl Groups on the Stereoselective Biotransformation of Methadone and its Interactions with P-Gp.

The stereo-selective metabolism of racemic $d_9$-methadone is determined using pooled human liver microsomes (Corning Gentest, Fisher Scientific, Pittsburgh, PA) and microsomes prepared from insect cells transfected with cDNAs encoding for human CYP2B6, 2D6, 2C9, 2C19, 3A4, and 3A5 (Corning Gentest, Fisher Scientific, Pittsburgh, PA) and compared to the stereo-selective metabolism of racemic methadone. The reaction components are as described above.

The effect of a range of methadone and $d_9$-methadone concentrations between 30 and 900 μM on the velocity of R/S-EDDP and R/S-$d_6$-EDDP formation are used to obtain the saturation curves necessary to calculate the apparent $K_m$ and $V_{max}$ for the reaction. The total volume of the reaction is 200 μl. The addition of an NADPH-regenerating system to the reaction mixture to initiate the reaction. Then the reaction components are shaken in a water bath at 37° C. for 30 min. The reactions are stopped by the addition of 1.2 mL of ice-cold acetonitrile. The reaction components are then centrifuged at 12,000×g for 10 min to precipitate proteins. The supernatant is evaporated at 40° C. under a $N_2$ stream and the residue is reconstituted in initial mobile phase. The concentrations of R-EDDP, S-EDDP, R-$d_6$-EDDP, and S-$d_6$-EDDP are analyzed by an LC-MS/MS method.

Sample analysis. Stereo-selective analysis of the enantiomers of $d_9$-methadone and nondeuterated methadone are analyzed with an LC-MS/MS method. A Thermo TSQ LC-MS/MS system can be used that consists of a Quantiva triple quadrupole mass spectrometer and Vanquish UHPLC system (Thermo Fisher Scientific, Waltham, MA). The system is controlled by Thermo Scientific Xcalibur Software (Version 4.1.31.9, Thermo Fisher Scientific, Waltham, MA). Separation of R- and S-methadone is achieved by a Phenomenex Lux® Cellulose-2 column (250×4.6 mm, 5 μm). The mobile phase is a premixed solution of hexane and ethanol (99:1, v/v) with 0.5% diethylamine. The flow rate is 1.0 mL/min and 300 μL of the eluent mobile phase is injected into the mass spectrometer via a "T" valve. Selected reaction monitoring (SRM) is set up at m/z 310→265 for the methadone enantiomers and at m/z 319→268 for the $d_9$-methadone enantiomers. Selected reaction monitoring for the metabolites of methadone and $d_9$-methadone is set up at m/z 278→249 for R- and S-EDDP and at 284→249 for R- and S-$d_6$-EDDP, respectively.

Data analysis and statistical analysis. Each reaction with each microsomal preparation is performed in duplicate and repeated six times. The data will be presented as the mean±standard deviation. Kinetic analysis is done by non-linear regression using GraphPad Prism v. 5.0 software (GraphPad Software, San Diego, CA). The $K_m$ and $V_{max}$ values of R- and S-methadone in the methadone racemic mixture to the respective $K_m$ and $V_{max}$ values of R- and S-$d_9$-methadone in the $d_9$-methadone racemic mixture will be compared. The results are analyzed using either an independent sample t-test or a non-parametric test, depending on the normality of distribution and equality of variances (SPSS software, v. 25, IBM). P-values<0.05 is considered statistically significant.

In order to assess the extent to which P-gp mediates the efflux of $d_9$-methadone in comparison to nondeuterated methadone, the uptake of the tested compounds is investigated in the hCMEC/D3 human brain microvascular endothelial cell line in the absence and presence of cyclosporine A (CsA), a known P-gp inhibitor. The expression (Poller et al., *Cellular and molecular neurobiology.* 30(1):63-70, 2010; Dauchy et al., *Biochemical pharmacology.* 77(5):897-909, 2009; Ohtsuki et al., *Molecular pharmaceutics.* 10(1):289-96, 2013) and functional activity of P-gp in hCMEC/D3 cells (Poller et al., *Cellular and molecular neurobiology.* 30(1):63-70, 2010; Tai et al., *Brain research.* 1292:14-24, 2009) has been previously reported and this cell line has been used as a human blood-brain barrier model to conduct transport studies (Poller et al., *Cellular and molecular neurobiology.* 30(1):63-70, 2010; Ragnaill et al., *European journal of pharmaceutics and biopharmaceutics: official journal of Arbeitsgemeinschaft fur Pharmazeutische Verfahrenstechnik eV.* 77(3):360-7, 2011) including in the laboratory of Dr. Rytting (Lopalco et al., *International journal of nanomedicine.* 10:1985-96, 2015). The hCMEC/D3 cells were obtained from Dr. Bickel, Texas Tech University Health Sciences Center, Amarillo, TX (with permission from Dr. Couraud, Inserm, Paris, France). Cells are cultured according to the protocol established in Dr. Rytting's laboratory until 80-90% confluent. At this point, 5 μM $d_9$-methadone or 5 nondeuterated methadone is administered in Hank's balanced salt solution (HBSS) containing 10 mM HEPES and 15 mM glucose at pH 7.4 and 37° C. To measure the baseline uptake, the hCMEC/D3 cells will be pre-incubated with 10 μM of CsA for 30 min in the uptake buffer and the same concentration of CsA are present during the uptake experiment (Wang et al., *International journal of pharmaceutics.* 288(2):349-59, 2005). The reaction is terminated at different time points by aspiration of the incubation buffer and washing the cells three times with cold uptake buffer. The cells are lysed with 0.5% Triton X-100 in 0.2N sodium hydroxide solution on ice. The uptake of $d_9$-methadone and of nondeuterated methadone is compared within the linear range of the reaction.

Sample analysis. The concentrations of $d_9$-methadone and nondeuterated methadone in the cellular lysates is determined by LC-MS/MS as described above and the data will be normalized for cellular protein content as determined by the BCA assay for each well.

Data analysis and statistical analysis. Each time point is performed in triplicate and repeated three times. The data will be presented as the mean±standard deviation. The following is compared: (1) the uptake of $d_9$-methadone and nondeuterated methadone in hCMEC/D3 cells, representing total uptake by the cells; (2) the uptake of $d_9$-methadone and nondeuterated methadone in hCMEC/D3 cells in the presence of the P-gp inhibitor CsA, representing the baseline uptake by the cells; (3) P-gp-mediated uptake, which is calculated as the difference between the baseline uptake and the total uptake for each of the substrates. The results are analyzed using either the independent sample t-test or a non-parametric test, depending on the normality of distribution and equality of variances (SPSS software, version 25, IBM). P-values less than 0.05 will be considered statistically significant.

Determine the Pharmacokinetic Profile as Well as the Acute Toxicity of $d_9$-Methadone.

Chemicals. Protein concentrations were measured using Bradford protein assay reagent (Bio-Rad Laboratories, Hercules, CA, USA) with bovine serum albumin as a standard. (±)-Methadone hydrochloride and (±)-$d_9$-methadone (1 mg/ml solution in methanol) were purchased from Sigma-Aldrich (St. Louis, MO, USA). All other chemicals were purchased from Sigma-Aldrich (St. Louis, MO) unless otherwise mentioned.

Animals. All experimental procedures were approved by the Animal Care and Use Committee at the University of Texas Medical Branch (UTMB) at Galveston and were in accordance with guidelines published by the US National Institutes of Health Guide for the Care and Use of Laboratory Animals (NTH Publication No. 85-23, revised 1996). Hsd:ICR (CD-1) mice were purchased from Envigo (Indianapolis, IN) and C57BL/6N mice (7-10 weeks, both sexes) were purchased from Charles River Laboratories (Houston, TX). All animals were housed in temperature-controlled rooms (23° C.) with a 12:12 hour light/dark cycle and with unlimited access to food and water in an American Association for Accreditation of Laboratory Animal Care (AAALAC)-accredited animal facility.

In vivo toxicity of $d_9$-methadone vs methadone. The toxicity of $d_9$-methadone and methadone administered intravenously (i.v.) via tail vein was assessed in CD-1 male mice using the Up-and-Down method (OECD/OCDE. OECD Guideline for Testing of Chemicals: Acute Oral Toxicity-Up-and-Down Procedure). Following the administration of the drug, each animal was observed for 20 minutes and scored using the Clinical Scores scale (1-5) as described in detail in our recent report (Fokina et al., *Journal of Biomedical Nanotechnology* 18(2):589-99, 2022). The toxicity of methadone was evaluated, for which the starting dose administered to the first animal was selected using a constant multiplicative factor of 1.2 and was five steps below 41 mg/kg; the latter value represented the LD50 of methadone which was administered intraperitoneally (i.p.) to Swiss mice (Hsia et al., *Science* 193(4252):498-500, 1976). The dose for the next animal was increased or decreased by a factor of 1.2 depending on whether the animal survived or died, respectively. The dosing was stopped when five reversals occurred in six animals tested consecutively. The estimated $LD_{50}$ value was calculated using the maximum likelihood method imbedded in the AOT425 software v.1.0 (Westat, Inc. and U.S. Environmental Protection Agency, Washington, DC). The outcome was deemed the same for all animals with the Clinical Score of 5 for those sacrificed by $CO_2$ asphyxiation for humane reasons and for those that had died during the testing. For $d_9$-methadone, a similar approach was used, however the starting dose was selected five steps above the $LD_{50}$ value that we determined for methadone.

Data indicated that the estimated $LD_{50}$ value for a single intravenous dose of methadone and $d_9$-methadone were 11.6 mg/kg, 95% CI (11.5, 13.4) and 24.8 mg/kg, 95% CI (20.6, 28.7), respectively.

Pharmacokinetic and tissue distribution of $d_9$-methadone vs methadone. The PK parameters of $d_9$-methadone and methadone were determined following the i.v. administration in CD-1 male mice. N=3 experiments were conducted for each studied compound. For the PK study, (±)-methadone hydrochloride was diluted in Dulbecco's phosphate buffered saline (DPBS, cell culture grade, Fischer Scientific, PA, USA) to achieve a final concentration of 0.5 mg/mL. To prepare (±)-$d_9$-methadone solution, 5 mL of the 1 mg/ml stock in methanol, then the dried residue was reconstituted in 3 ml of 20 mM hydrochloric acid, and then PBS was added to achieve a final concentration of 0.5 mg/ml of $d_9$-methadone. At the day of each experiment, each mouse (n=9 animals per experiment) received a 2 mg/kg dose of $d_9$-methadone or methadone i.v. via tail vein. The dosage volume was adjusted based on a body weight of each mouse and was equivalent to 100 μL of the drug solution administered to a mouse weighing 25 g. At predetermined time points (5 min, 15 min, 30 min, 1 h, 2 h, 3 h, 4 h, 6 h, and 8 h), n=1 animal was sacrificed by $CO_2$ asphyxiation. The blood samples were obtained by cardiac puncture and centrifuged immediately to separate the plasma. The lungs, liver, spleen, heart, and a kidney were resected from each animal and weighed (for paired organs, both lungs were collected and processed together, while only one kidney was harvested from each animal). The plasma samples and the organs were stored at −80° C. until analysis.

Tissue sample preparation. After thawing, the organs were weighed and homogenized with deionized water containing 1% formic acid. The ratios of the organ weight to the volume of deionized water (w/v) in the homogenates were: 1:1 for the brain, 1:3 for the liver, heart, lungs and kidney, and 1:4 for the spleen.

Sample Analysis. A liquid chromatography-mass spectrometry (LC-MS/MS) method for the quantification of methadone, $d_9$-methadone, EDDP and $d_6$-EDDP was developed and validated. The samples were analyzed with a Thermo Scientific™ TSQ Quantiva™ Triple Quadrupole mass spectrometer (Waltham, MA). The system was controlled by Xcalibur 3.0 software. Separation of the analytes was achieved by a Waters Symmetry $C_{18}$ HPLC column at 45° C. The mobile phase was made of (A) acetonitrile and (B) 0.1% formic acid aqueous solution (v/v) with gradient elution of 0-5 min, 25% A to 50% A with a flow rate of 350 μL/min. Before each injection, the HPLC column was washed with 90% A, and then equilibrated with 25% A for 5 min. The following internal standards were utilized: $d_9$-methadone (for quantitative determination of methadone), methadone (for $d_9$-methadone), and $d_3$-EDDP (for EDDP). Due to the unavailability of synthesized $d_6$-EDDP as a standard compound, $d_3$-EDDP was used in lieu of $d_6$-EDDP to construct a calibration curve, with EDDP serving as internal standard. Multiple reaction monitoring (MRM) was set up at m/z 310→265 for methadone, m/z 319→268 for $d_9$-methadone, m/z 278→249 for EDDP, m/z 284→249 for $d_6$-EDDP, and m/z 281→249 for $d_3$-EDDP.

The samples of plasma and tissue collected from the mice were processed as follows: 250 μL of plasma or 200 μL of organ homogenates were spiked with 10 μL of the corresponding internal standard working solution and 10 μL of $Li_2CO_3$ (10 mg/ml stock), and then the mixture was vortexed for 30 sec. Afterwards, 800 μL of acetonitrile was added and vortexed for 30 sec. The mixture was centrifuged at 12,000×g for 15 min, and then the supernatant was transferred to a 2-mL centrifuge tube and dried at 50° C. under a stream of nitrogen. The residue was reconstituted with 150 μL of initial mobile phase and centrifuged at 12,000×g for 5 min. 100 μL of the supernatant was transferred to an HPLC injection vial and 10 μL of the sample was injected into the LC-MS/MS system.

The calibration and quality control standards of methadone, $d_9$-methadone, EDDP and $d_3$-EDDP (in lieu of $d_6$-EDDP) were prepared by spiking the appropriate working solution of the standards with the blank plasma or the tissue homogenates, and the samples were processed as described above. The calibration curves for methadone, $d_9$-methadone, EDDP and $d_3$-EDDP were found to be linear in the ranges of 3.0-2400 ng/mL in plasma, 5.0-3900 ng/g in brain, 18.0-14000 ng/g in spleen, and 14.0-12000 ng/g in liver, kidney, lung and heart samples. The intra- and inter-day accuracy of the method was within 90% to 114%, and the precision was above 93%. All biological samples were processed and analyzed along with quality control samples at high, medium and low concentration levels.

Pharmacokinetic analysis. The PK parameters for methadone, $d_9$-methadone, and their metabolites EDDP and $d_6$-EDDP were determined using Kinetica software (v. 5.1, Thermo Fisher Scientific, Waltham, MA). The maximum plasma concentration ($C_{max}$) and time to $C_{max}$ ($T_{max}$) were determined by visual inspection of the concentration versus time curve for which the data for each experiment utilized multiple mice (one mouse per time point, total of n=3 experiments). The area under the plasma concentration vs. time curve over the 8-hour study period ($AUC_{0-8h}$) was determined by non-compartmental analysis, utilizing the trapezoidal method. For methadone and $d_9$-methadone, the clearance (CL) was calculated as the dose divided by the $AUC_{0-\infty}$, with the $AUC_{0-\infty}$ being calculated as the $AUC_{0-8h}$ plus an extrapolated $AUC_{8h-\infty}$ predicted as the concentration at 8 h divided by the terminal rate constant fit through the latter time points. The total volume of distribution ($V_{ss}$) was calculated as the clearance multiplied by the mean residence time, which is the $AUC_{0-\infty}$ divided by the area under the moment curve ($AUMC_{0-\infty}$). The half-life was calculated as ln(2) divided by the terminal rate constant. The $AUC_{0-8h}$ for the parent drugs and their respective metabolites in each studied organ were derived using time vs. tissue concentration data from multiple mice (one animal per time point, total of n=3 experiments).

FIG. 3A-3D show the plasma concentrations of methadone and $d_9$-methadone and their corresponding metabolites EDDP and $d_6$-EDDP as a function of time following i.v. administration of the studied drugs in male CD-1 mice. The plasma concentrations of both methadone and $d_9$-methadone declined in a biexponential manner; the calculated PK parameters are presented in Table 2. The exposure to $d_9$-methadone ($AUC_{0-8h}$) and the $C_{max}$ of $d_9$-methadone exceeded those of methadone by 6 folds (P<0.05) and 4 folds (P<0.0001), respectively. The $V_{ss}$, and CL values of $d_9$-methadone were reduced by 8 and 5 folds (P<0.01), respectively, as compared to methadone, while the difference in the elimination half-lives for both drugs did not attain statistical significance. EDDP and $d_6$-EDDP, the corresponding metabolites of methadone and $d_9$-methadone, were determined in the plasma of mice over the entire study period FIG. 3C and FIG. 3D. The $C_{max}$ of $d_6$-EDDP in plasma was 5-fold lower than the $C_{max}$ of EDDP (P<0.001), while the difference between the $T_{max}$ values of the metabolites did not attain statistical significance (Table 2). The $AUC_{0-8h}$ of $d_6$-EDDP was 2-fold lower than the $AUC_{0-8h}$ of EDDP (P<0.01).

TABLE 2

Pharmacokinetic parameters of methadone and $d_9$-methadone, and their respective metabolites, EDDP and $d_6$-EDDP, in the plasma of male CD-1 mice after a single intravenous injection of the studied drugs.

| Parent Drug Parameters | Methadone | $d_9$-Methadone | P-value |
|---|---|---|---|
| Dose (mg/kg) | 2.0 | 2.0 | — |
| Cmax (ng/mL) | 521 ± 55 | 2270 ± 181 | 0.0001 |
| Tmax (h) | 0.08 ± 0 | 0.08 ± 0 | — |
| $AUC_{0-8\ h}$ (ng · h/mL) | 414 ± 67 | 2362 ± 785 | 0.0128 |
| $AUC_{0-\infty}$ (ng · h/mL) | 436 ± 75 | 2389 ± 817 | 0.0146 |
| CL (L/h/kg) | 4.7 ± 0.8 | 0.9 ± 0.3 | 0.0019 |
| $V_{ss}$ (L/kg) | 8.9 ± 2.0 | 1.2 ± 0.0 | 0.0028 |
| Half-life (h) | 2.2 ± 0.8 | 1.1 ± 0.2 | 0.0796 |
| **Metabolite Parameters** | **EDDP** | **$d_6$-EDDP** | **P-value** |
| Cmax (ng/mL) | 233 ± 28 | 48 ± 7 | 0.0004 |
| Tmax (h) | 0.14 ± 0.10 | 0.33 ± 0.14 | 0.1242 |
| $AUC_{0-8\ h}$ (ng · h/mL) | 257 ± 29 | 138 ± 25 | 0.0058 |

Methadone and $d_9$-methadone, and their respective metabolites, EDDP and $d_6$-EDDP, were quantified in the plasma samples of male CD-1 mice following a single intravenous injection of 2.0 mg/kg of the parent drug. The plasma concentration-time profiles of the drugs and their metabolites are shown in FIG. 2. The PK parameters were determined using Kinetica software (v. 5.1). The data are presented as the mean ± s.d. of three experiments. EDDP, 2-ethylidene-1,5-dimethyl-3,3,-diphenylpyrrolidine.

The ratio of the $AUC_{0-8h}$ of the metabolite to the $AUC_{0-8h}$ of the parent drug was lower for $d_9$-methadone (0.06±0.01) than for methadone (0.62±0.04, P<0.0001).

Following i.v. administration of the studied drugs, the extent of the exposure of the organs to $d_9$-methadone ranked as following: lungs>kidneys≈liver>spleen>heart>brain, while the rank order for methadone was: kidneys≈lungs>spleen>liver>heart>brain. The exposure of the lungs and liver of the mice to $d_9$-methadone was greater than the exposure to methadone, while the exposure of the heart, kidneys, and spleen to $d_9$-methadone was lower than that of methadone (Table 3, P<0.05). For all the results of the PK and tissue distribution experiments that were statistically significant by the standards of this study, the achieved statistical power was above 0.85 at $\alpha$=0.05.

TABLE 3

$AUC_{0-8\ h}$ of methadone, $d_9$-methadone, and their respective metabolites EDDP and $d_6$-EDDP in organs of male CD-1 mice after a single intravenous injection of 2.0 mg/kg of either methadone or $d_9$-methadone.

| Parent Drug Tissue $AUC_{0-8\ h}$ (ng · h/g) | Methadone | $d_9$-Methadone | P-value |
|---|---|---|---|
| Brain | 877 ± 395 | 780 ± 73 | 0.6971 |
| Liver | 3272 ± 570 | 5052 ± 117 | 0.0061 |
| Lung | 7694 ± 460 | 10799 ± 969 | 0.0074 |
| Heart | 1890 ± 115 | 1426 ± 230 | 0.0351 |
| Kidney | 7784 ± 469 | 5110 ± 408 | 0.0017 |
| Spleen | 4841 ± 494 | 3451 ± 148 | 0.0095 |
| **Metabolite Tissue $AUC_{0-8\ h}$ (ng · h/g)** | **EDDP** | **$d_6$-EDDP** | **P-value** |
| Brain | 8.96 ± 5.26 | <LLOQ§ | <0.05 |
| Liver | 5608 ± 218 | 4375 ± 513 | 0.0186 |
| Lung | 9672 ± 856 | 9886 ± 614 | 0.7433 |
| Heart | 2155 ± 144 | 1243 ± 254 | 0.0057 |
| Kidney | 2815 ± 226 | 1562 ± 207 | 0.0021 |
| Spleen | 622 ± 45 | 411 ± 33 | 0.0028 |

The data reflect the exposure of individual organs to the parent drug and its metabolite and are presented as the mean ± s.d. of three experiments.

§The concentration of $d_6$-EDDP in the brain was below the lower limit of quantitation at every time point for all three animals. AUC, area under the tissue concentration vs. time curve; EDDP, 2-ethylidene-1,5-dimethyl-3,3,-diphenylpyrrolidine; LLOQ, lower limit of quantification.

The ratios of $AUC_{0-8h}$ in the organs to the $AUC_{0-8h}$ in the plasma indicated substantial distribution and exposure of the mouse organs to methadone in comparison to reduced distribution ratios for $d_9$-methadone (FIG. 4, P<0.01 for all organs). Despite similar exposure of the brain to $d_9$-methadone and methadone (as reflected by similar AUC values), the brain-to-plasma AUC ratio of $d_9$-methadone was 0.35±0.12 while the brain-to-plasma AUC ratio for methadone was 2.05±0.62 (FIG. 4, P<0.01), suggesting lower proportional transfer of $d_9$-methadone across the blood-brain barrier (BBB).

The extent of the exposure of the organs to $d_6$-EDDP and EDDP, the respective metabolites of $d_9$-methadone and methadone, ranked as follows: lungs>liver>kidney≈heart>spleen. The exposure of the lungs to $d_6$-EDDP and EDDP was similar, while the exposure to $d_6$-EDDP in the liver, heart, kidney and spleen was significantly lower than the exposure to EDDP (Table 3, P<0.05). The concentration of $d_6$-EDDP in the brain was below the lower limit of quantification (LLOQ).

Determine the Analgesic Efficacy of $d_9$-Methadone.

Animal models of pain. To model postoperative pain in mice, plantar incision was performed under isoflurane anesthesia. Specifically, a 4-8 mm incision was made through the skin, fascia, and muscle of the plantar side of one hind paw, longitudinally starting from the proximal edge of the heel. The skin was apposed with sutures (Fine Science Tools, Foster City, CA). The suture was removed at the end of postoperative day 2. To model neuropathic pain in mice, a surgery was performed to ligate the fifth lumbar (L5) spinal nerve (spinal nerve ligation, SNL).

Behavioral testing. Mechanical pain sensitivity after plantar incision or SNL was assessed by measuring paw withdrawal behaviors in response to von Frey filament (VFF) probing. A mouse was placed in a plastic chamber on top of a mesh screen platform. The VFF of 0.98 mN was applied perpendicularly to the hind paw. At baseline (i.e., before surgery), mice rarely withdraw their hind paw from this VFF probing, whereas after surgery, the operated hind paw develops nociceptive hypersensitivity manifested as the increased number of withdrawals from ten trials of probing (Hankerd et al., *Pain* 163(3):461-73, 2022; La et al., *Mot Pain* 13:1744806917713907, 2017). The percent of withdrawal responses out of the ten trials was recorded.

Methadone (3 mg/kg) or $d_9$-methadone (3 mg/kg) was administered i.p. either once before plantar incision (i.e., intraoperative treatment), repeatedly at 4-hour, 1-day, 2-day, and 3-day time points post-surgery (i.e., postoperative treatments), or repeatedly at 3-day, 4-day, and 5-day time points post-SNL. In a separate experiment that included the postoperative treatment, naloxone methiodide (NLXM, 10 mg/kg) was injected i.p. 30 minutes before the administration of either methadone or $d_9$-methadone at 1-day post-surgery.

Statistical analysis. We used a generalized linear mixed model to analyze the number of withdrawals out of 10 trials (binomial distribution) repeatedly measured at multiple time points (AR1 covariance structure) with random intercepts for subject (i.e., mouse) variances. Degrees of freedom were allowed to vary across tests by Satterthwaite approximation.

For sample size calculation in the behavioral study, preliminary experiments were conducted using three mice of plantar incision model in each of intra- and post-operative treatment regimens (both sexes at 1:2 ratio). The preliminary intra-operative treatment resulted in the Cohen's d value of 2.1 between the methadone and $d_9$-methadone groups in comparing the % of withdrawals measured 4 hours post-incision, indicating that at least five mice per group are needed to achieve statistical power of 0.8 at $\alpha$=0.05 in this experimental setup (both sexes at 2:3 ratio). In the postoperative treatment experiment comparing % withdrawals before and after the treatment with $d_9$-methadone (i.e., a paired comparison), Cohen's d was >20, requiring at least two mice per group for the statistical power of 0.80 at $\alpha$=0.05. Thus, n=3 mice were used per group for this experimental design (both sexes at 1:2 ratio).

Figure 5:
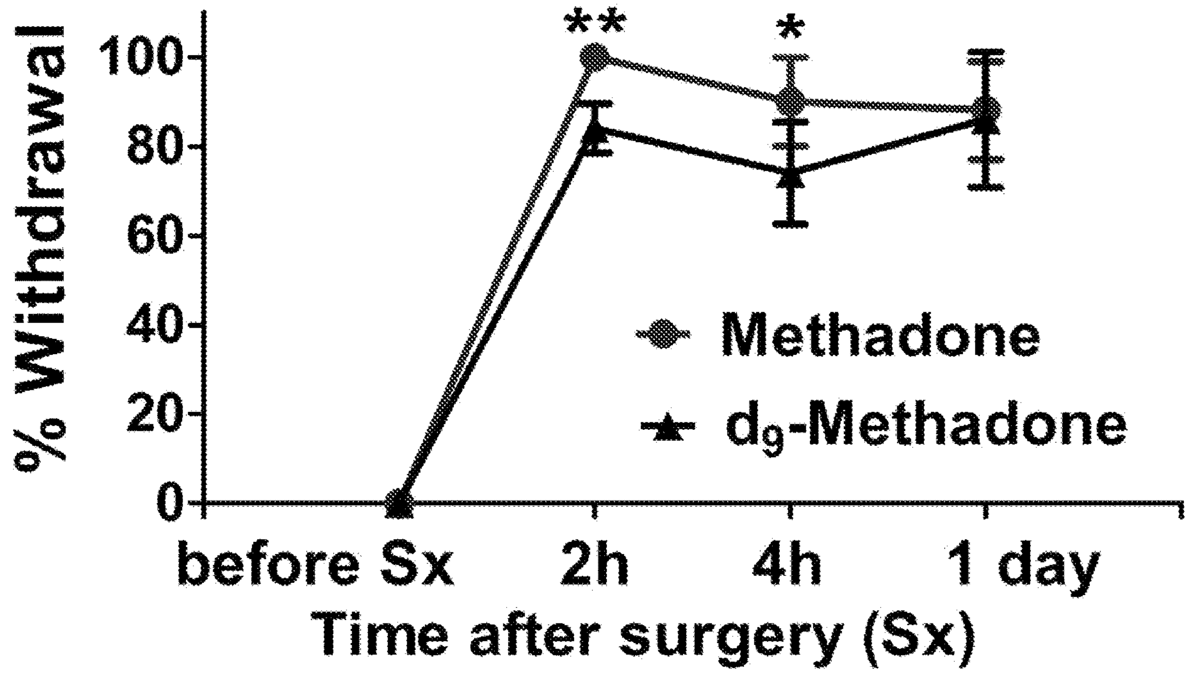
FIG. 5. The magnitude of postoperative mechanical pain hypersensitivity after intra-operative treatment with methadone or $d_9$-methadone. Using an intra-operative regimen, we tested if $d_9$-methadone produces greater relief of postoperative pain than methadone. Under anesthesia, immediately before plantar incision, mice received either methadone or $d_9$-methadone (3 mg/kg, i.p.) as an intra-operative treatment. Data are presented as the mean±s.d. of 3 experiments. N=3 animals were used for each time point. *P<0.05; **P<0.01.

Methadone has been shown to decrease postoperative pain with either intra- or post operative treatment regimens (Kharasch, *Anesth Analg* 112(1):13-6, 2011; Gottschalk et al., *Anesth Analg* 112(1):218-23, 2011; Neto et al., *J Anesth* 28(4):505-10, 2014). As shown in FIG. 5, mice treated with 3 mg/kg of $d_9$-methadone demonstrated lower postoperative mechanical hypersensitivity on the day of surgery than methadone-treated mice (t(17)=3.37, P=0.004 at 2 hr; t(17)=2.33, P=0.033 at 4 hr). On the next day, however, there was no difference in the degree of postoperative mechanical hypersensitivity between the two groups (t(17)=0.33, P=0.75).

Figure 6A:
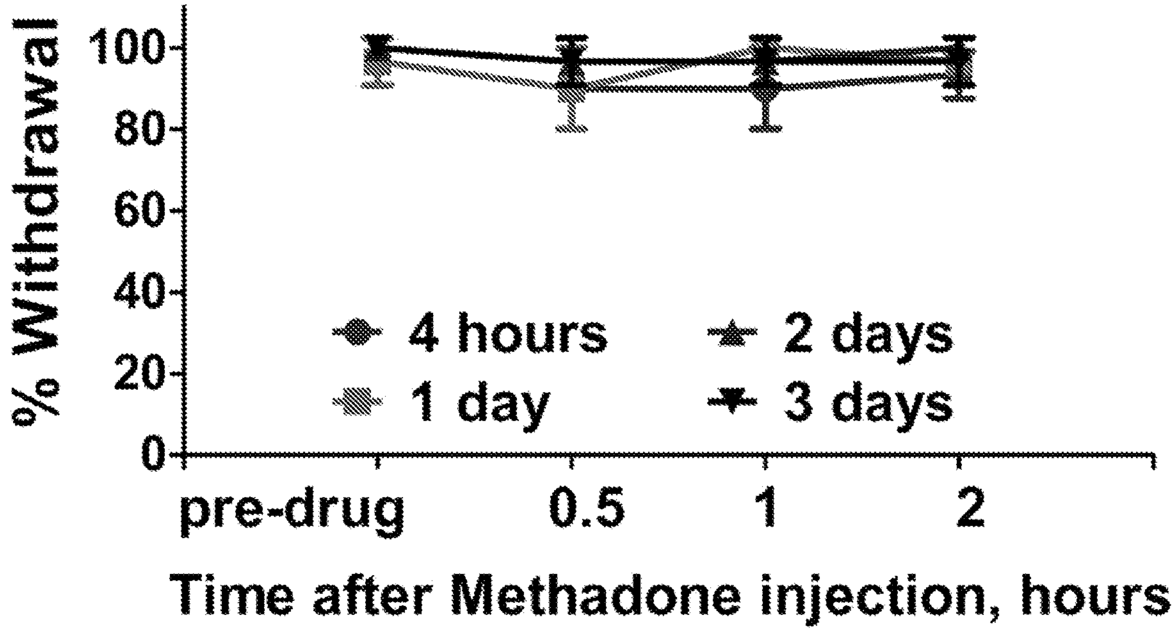
FIG. 6A-6C. The magnitude of post-operative mechanical pain hypersensitivity after post-operative treatment. Using a post-operative regimen, we tested if $d_9$-methadone produces greater relief of postoperative pain than methadone. After plantar incision, mice received 3 mg/kg, i.p., of either (A) methadone or (B) $d_9$-methadone as a post-operative treatment. (C) Effect of naloxone methiodide (NLXM), a peripherally restricted opioid receptor antagonist, on the magnitude of post-operative mechanical pain hypersensitivity produced by $d_9$-methadone. NLXM was administered post-operatively and 30 minutes prior to $d_9$-methadone injection. NLXM completely blocked the effect of $d_9$-methadone Data are presented as the mean±s.d. of 3 experiments. N=3 animals were used for each time point.
Figure 6B:
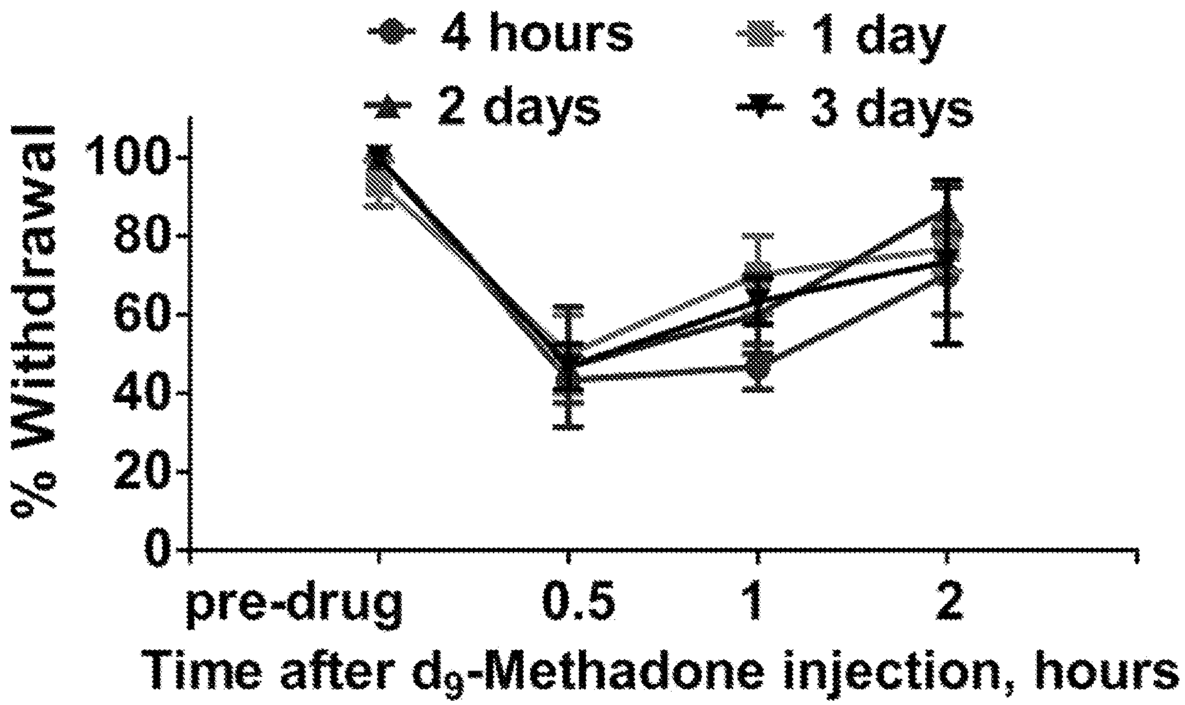

Methadone given postoperatively at a dose of 3 mg/kg was unable to reduce the postoperative mechanical hypersensitivity (FIG. 6A). On the other hand, the same dose of $d_9$-methadone alleviated hypersensitivity after each systemic injection once daily for 4 days (FIG. 6B: F(3,22)=18.1, P<0.001 between times post-injection). Of note, no development of the apparent analgesic tolerance was observed in the 'once daily for 4 days' treatment regimen applied in this study (F(3,20)=0.335, P=0.8 between treatment days).

Figure 6C:
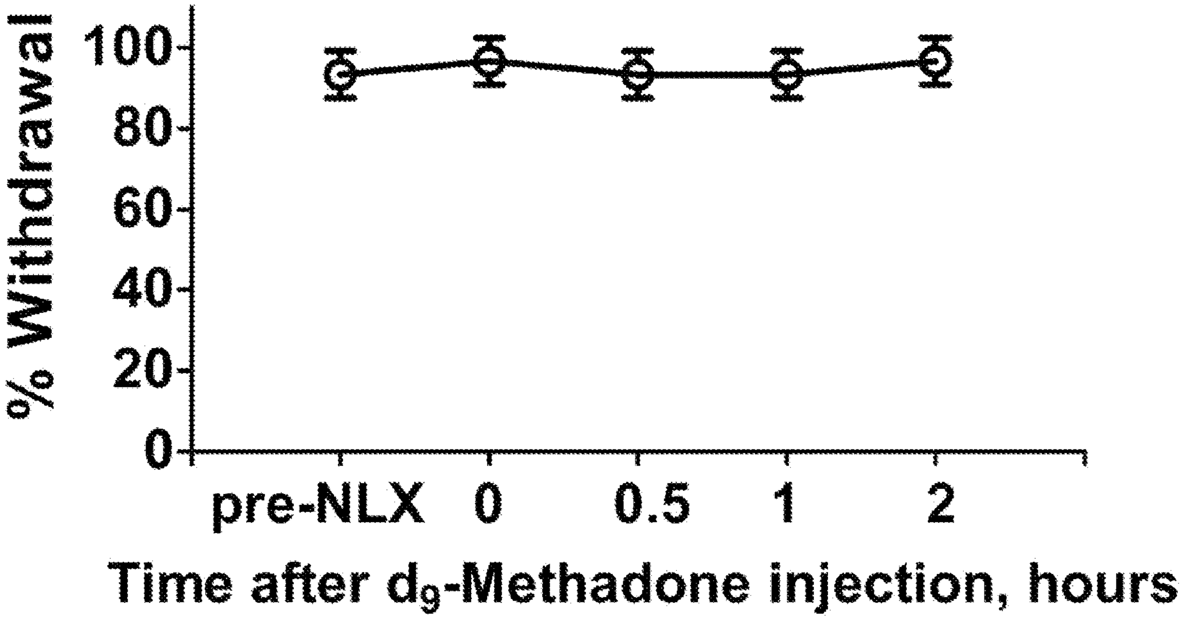

As methadone's analgesic effect is stringently mediated by opioid receptors in the periphery (He et al., *J Pain* 10(4):369-79, 2009), next it was investigated if the relief of postoperative pain by $d_9$-methadone would be similarly mediated by peripheral opioid receptors. Naloxone methiodide (NLXM), a peripherally restricted opioid receptor antagonist, was administered to the operated animals 30 minutes before the treatment with $d_9$-methadone. As a result, NLXM completely blocked the effect of $d_9$-methadone (FIG. 6C).

Figure 7:
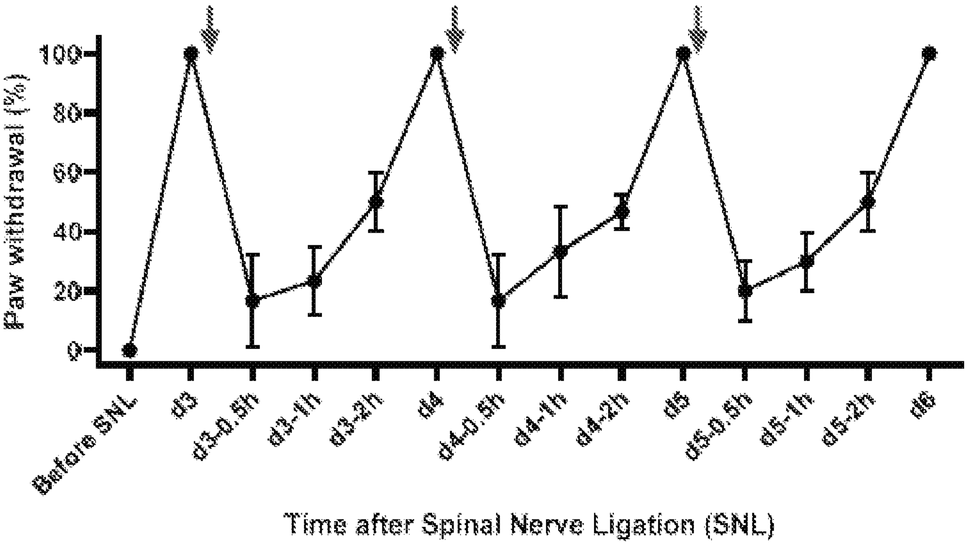
FIG. 7. The magnitude of neuropathic mechanical pain hypersensitivity after $d_9$-methadone treatment. After a surgery damaging peripheral nerves (spinal nerve ligation, SNL), mice developed tactile allodynia, a sign of neuropathic pain. Deuterated methadone ($d_9$-methadone, 3 mg/kg, i.p.) effectively inhibited this neuropathic pain after each injection. Data are presented as mean±SD, n=3 mice.

After the SNL surgery directly damaging peripheral nerves, mice developed tactile allodynia, a sign of neuropathic pain. Administration of $d_9$-methadone (3 mg/kg, i.p; arrow in FIG. 7) once daily for 3 days effectively alleviated this neuropathic pain after each injection (F(3,18)=13.0, P<0.001 between times post-injection). Of note, no development of the apparent analgesic tolerance was observed in the 'once daily for 3 days' treatment regimen applied in this study (F(2,22)=0.0, P=1.0 between treatment days).

Determine the Abuse Liability of $d_9$-Methadone.

Animals. Naïve mice were used for this study.

Experimental approaches. The abuse liability of $d_9$-methadone was assessed in the CPP behavioral paradigm primarily using a biased, 2-day drug-pairing design. Specifically, one day after measuring natural place preference, vehicle was be given in the morning, and the mouse was placed in its preferred chamber for 20 min. In the afternoon, test drugs were given, and the mouse was placed in its non-preferred chamber for 20 min. This conditioning procedure was repeated 2 times. One day after the last conditioning session, CPP for the drug-paired chamber was measured for 20 min.

Figure 8:
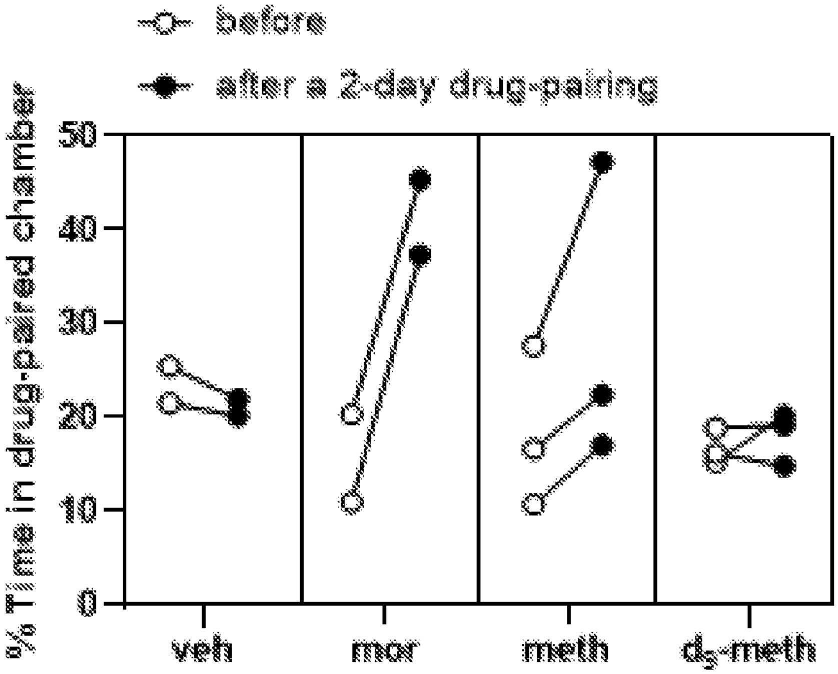
FIG. 8. Assessment of the abuse liability of analgesics using the conditioned place preference (CPP) paradigm. Mice developed CPP for a chamber paired with morphine (mor) or methadone (meth) after a 2-day conditioning, indicating the rewarding property of the drugs. However, mice did not develop CPP for a chamber paired with $d_9$-methadone ($d_9$-meth).

When a 3-chamber CPP box (one bright and one dark chamber connected by a smaller gray chamber) was used, mice preferred the dark chamber, staying only ~20% of time in the bright chamber during the first (baseline) free exploration session. However, mice that associated morphine (i.p.) with the bright chamber after a 2-day conditioning spent significantly more time in the bright chamber. In the same conditioning paradigm, mice that received $d_9$-methadone did not develop conditioned place preference for the drug-paired chamber (FIG. 8). Circles indicate individual mice before and after the 2-day drug-pairing conditioning.

The invention claimed is:

1. A method for treatment of pain in a subject comprising: administering a deuterated methadone having the structure of Formula I Formula I

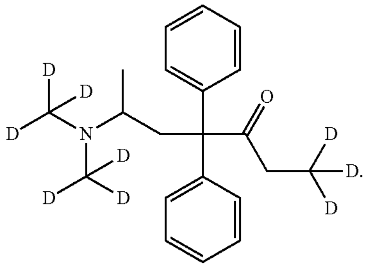

2. A method according to claim 1, wherein the compound is administered orally, nasally, transcutaneously, subcutaneously, intramuscularly, intravenously, intrathecaly or epidurally, sublingually, transbuccally, transsclerolly, or intraosseously.

3. A method according to claim 1, wherein the compound is formulated in a composition that further comprises a pharmacologically effective amount of an opioid antagonist.

4. A method according to claim 3, wherein the opioid antagonist is naloxone or naltrexone.

5. A method according to claim 1, wherein the compound is formulated in a composition that further comprises a nonopioid component or its pharmaceutically acceptable salts.

6. A method according to claim 1, wherein the pain is both neuropathic and somatic in origin.

7. A method according to claim 1, wherein the subject is a mammal.

8. A method according to claim 7, wherein the mammal is a human.

9. A method for treatment of addiction in a subject comprising: administering a deuterated methadone having the structure of Formula I Formula I

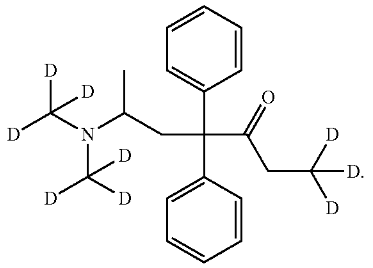

10. A method according to claim 9, wherein the compound is administered orally, nasally, transcutaneously, subcutaneously, intramuscularly, intravenously, intrathecally or epidurally, sublingually, transbuccally, transsclerolly, or intraosseously.

11. A method according to claim 10, wherein the compound is formulated in a composition that further comprises a pharmacologically effective amount of an opioid antagonist.

12. A method according to claim 11, wherein the opioid antagonist is naloxone or naltrexone.

13. A method according to claim 9, wherein the compound is formulated in a composition that further comprises a nonopioid component or its pharmaceutically acceptable salts.

14. A method according to claim 9, wherein the subject is a mammal.

15. A method according to claim 14, wherein the mammal is a human.

* * * * *